United States Patent
Sano et al.

(10) Patent No.: US 8,308,648 B2
(45) Date of Patent: Nov. 13, 2012

(54) ELECTRONIC BLOOD PRESSURE MEASUREMENT DEVICE CALCULATING BLOOD PRESSURE VALUE

(75) Inventors: Yoshihiko Sano, Kyoto (JP); Akihisa Takahashi, Kyoto (JP); Shingo Yamashita, Kyoto (JP); Yukiya Sawanoi, Nara (JP)

(73) Assignee: Omron Healthcare Co., Ltd., Kyoto-shi (JP)

( * ) Notice: Subject to any disclaimer, the term of this patent is extended or adjusted under 35 U.S.C. 154(b) by 1075 days.

(21) Appl. No.: 12/095,658

(22) PCT Filed: Nov. 22, 2006

(86) PCT No.: PCT/JP2006/323288
§ 371 (c)(1),
(2), (4) Date: May 30, 2008

(87) PCT Pub. No.: WO2007/072647
PCT Pub. Date: Jun. 28, 2007

(65) Prior Publication Data
US 2009/0312651 A1 Dec. 17, 2009

(30) Foreign Application Priority Data
Dec. 20, 2005 (JP) ................................ 2005-366029

(51) Int. Cl.
*A61B 5/02* (2006.01)
(52) U.S. Cl. ...................................... 600/493; 600/492
(58) Field of Classification Search .................. 600/493, 600/490, 495, 494, 492; 606/201, 202, 203
See application file for complete search history.

(56) References Cited

U.S. PATENT DOCUMENTS

| 5,865,756 A | 2/1999 | Peel, III |
| 6,224,558 B1* | 5/2001 | Clemmons ..................... 600/490 |
| 6,309,359 B1 | 10/2001 | Whitt et al. |
| 2002/0111554 A1* | 8/2002 | Drzewiecki et al. .......... 600/490 |

(Continued)

FOREIGN PATENT DOCUMENTS
EP   1 264 573   12/2002
(Continued)

OTHER PUBLICATIONS

European Search Report mailed May 25, 2011, directed to Application No. 06833110.7; 4 pages.

(Continued)

*Primary Examiner* — Michael Kahelin
*Assistant Examiner* — Tho Tran
(74) *Attorney, Agent, or Firm* — Morrison & Foerster LLP

(57) ABSTRACT

A blood pressure measurement bladder (50) has a predetermined amount of air introduced and sealed therein. A CPU (30) measures in advance the P-V property. The blood pressure measurement bladder (50) is wrapped around a measurement site. By exerting pressure from the outer side to the blood pressure measurement bladder (50), the internal pressure in the blood pressure measurement bladder (50) is increased to exert pressure on the blood vessel. During this process, the cuff pressure in the blood pressure measurement bladder (50) generated by volumetric change of the blood vessel by changing the pressure exerted from the outer side to the blood pressure measurement bladder (50), and the pressure pulse wave data are detected. By adding the cuff compliance property obtained by the P-V property that was measured in advance to the detected data as a correction value of the pressure pulse wave, blood pressure is calculated.

6 Claims, 16 Drawing Sheets

U.S. PATENT DOCUMENTS

| | | |
|---|---|---|
| 2003/0097074 A1 | 5/2003 | Oka et al. |
| 2004/0024325 A1 | 2/2004 | Nishibayashi et al. |
| 2005/0171445 A1 | 8/2005 | Millay et al. |
| 2005/0182332 A1 | 8/2005 | Sano et al. |
| 2009/0312651 A1 | 12/2009 | Sano et al. |

FOREIGN PATENT DOCUMENTS

| | | |
|---|---|---|
| EP | 1 967 133 | 9/2008 |
| JP | 05-269089 | 10/1993 |
| JP | 5-329113 T1 | 12/1993 |
| JP | 11-309119 | 11/1999 |
| JP | 11-318835 | 11/1999 |
| JP | 2003-144399 | 5/2003 |
| JP | 2005-230175 | 9/2005 |
| RU | 2 063 698 | 7/1996 |
| SU | 176366 | 1/1965 |
| WO | WO-01/95798 | 12/2001 |
| WO | WO-2007/072647 | 6/2007 |

OTHER PUBLICATIONS

International Search Report mailed Dec. 19, 2006, directed to counterpart international application No. PCT/JP2006/323288; 1 page.

Japanese Decision to Grant Patent mailed on Feb. 9, 2010, directed to counterpart Japanese Patent Application No. 2005-366029; 6 pages.

Russian Decision on Grant a Patent for Invention mailed on Feb. 18, 2010, directed to counterpart Russian Patent Application No. 2008129706/14(036802); 15 pages.

* cited by examiner

FIG.1
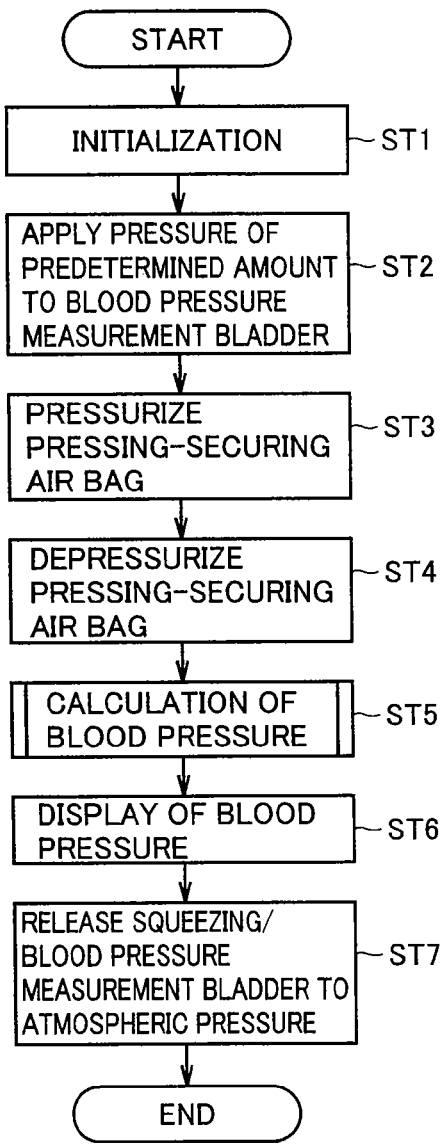
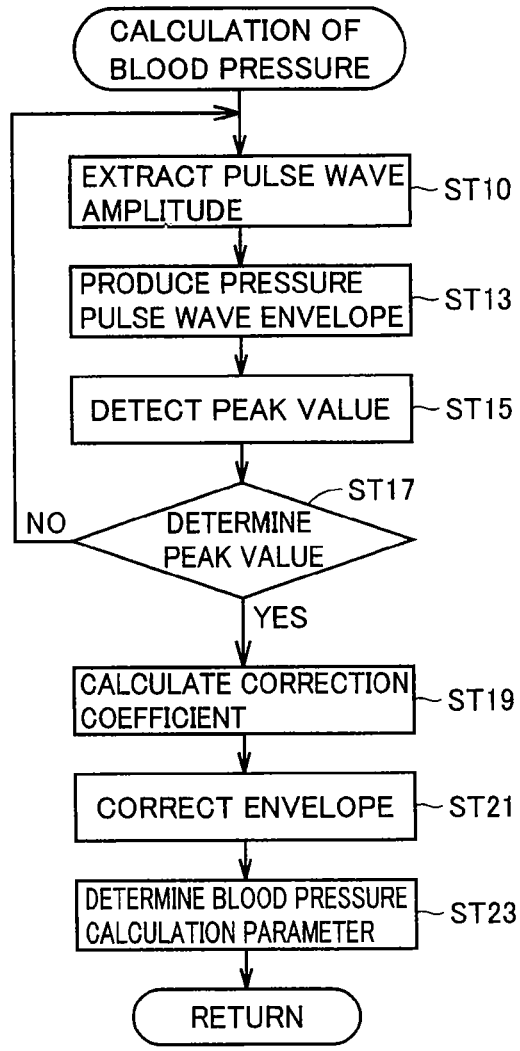

FIG.4
(A)
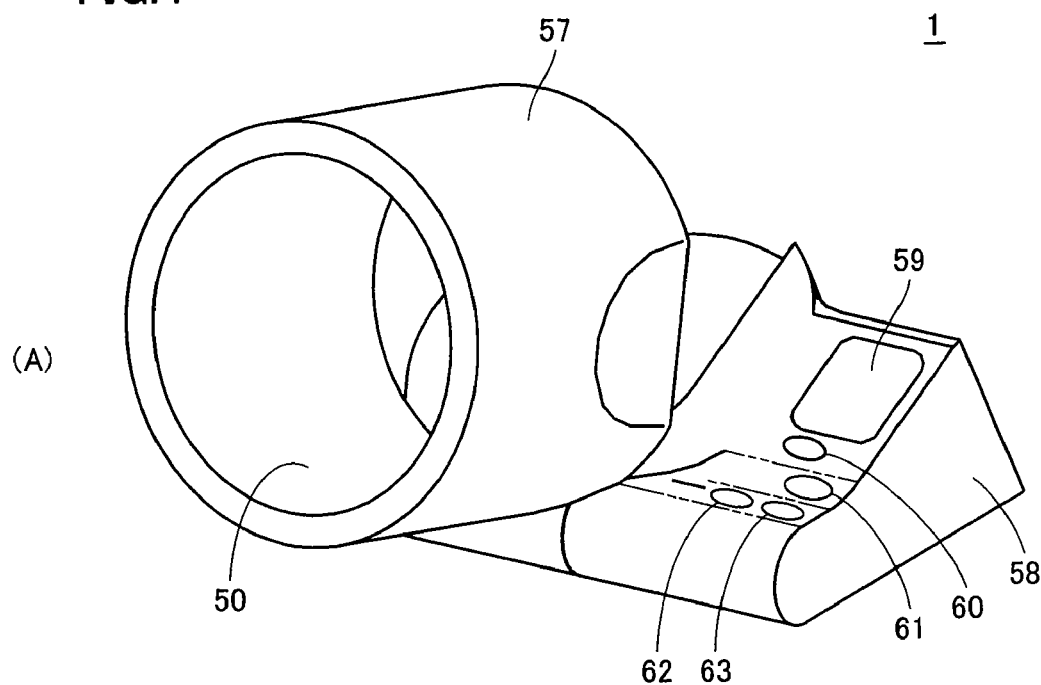
(B)
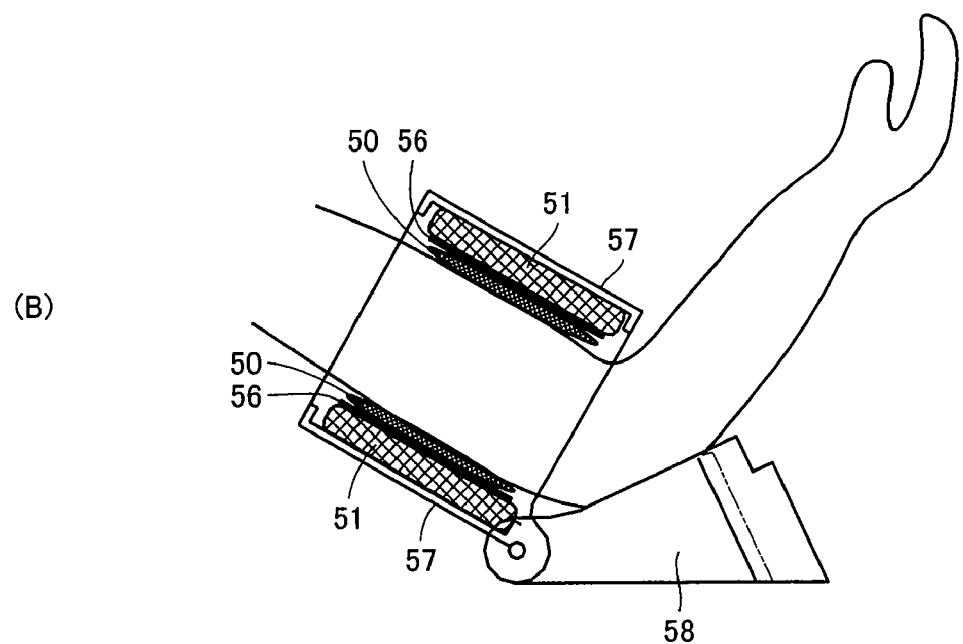

BLOOD PRESSURE MEASUREMENT MODE
(DEPRESSURIZE MEASUREMENT)

FIG.8 WHEN MEASUREMENT ENDS

FIG.15
WHEN ARM SIZE DIFFERS
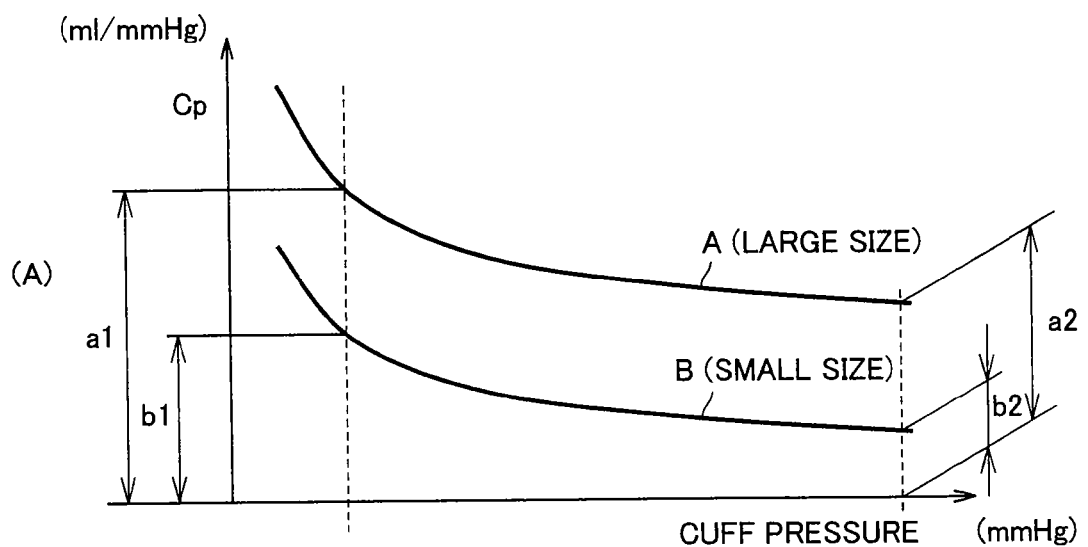
(A)
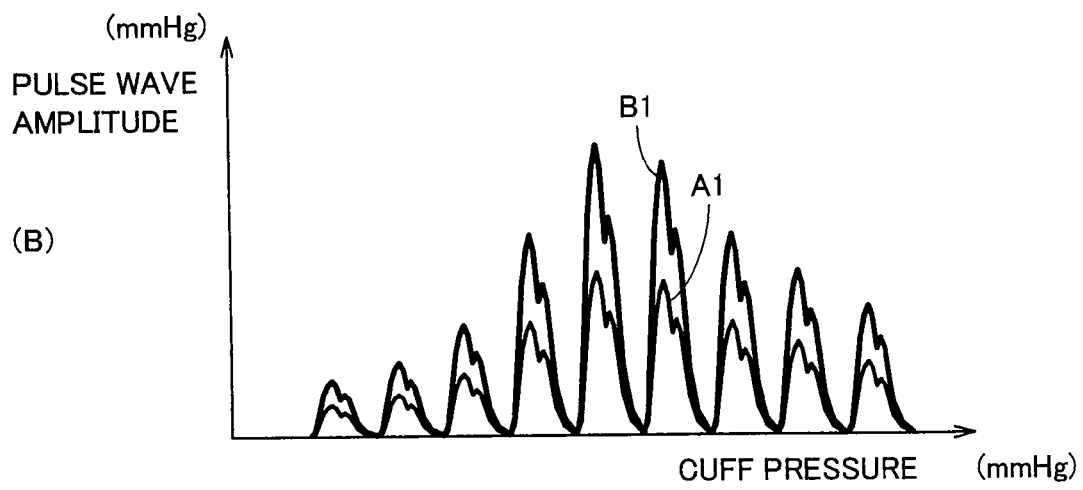
(B)

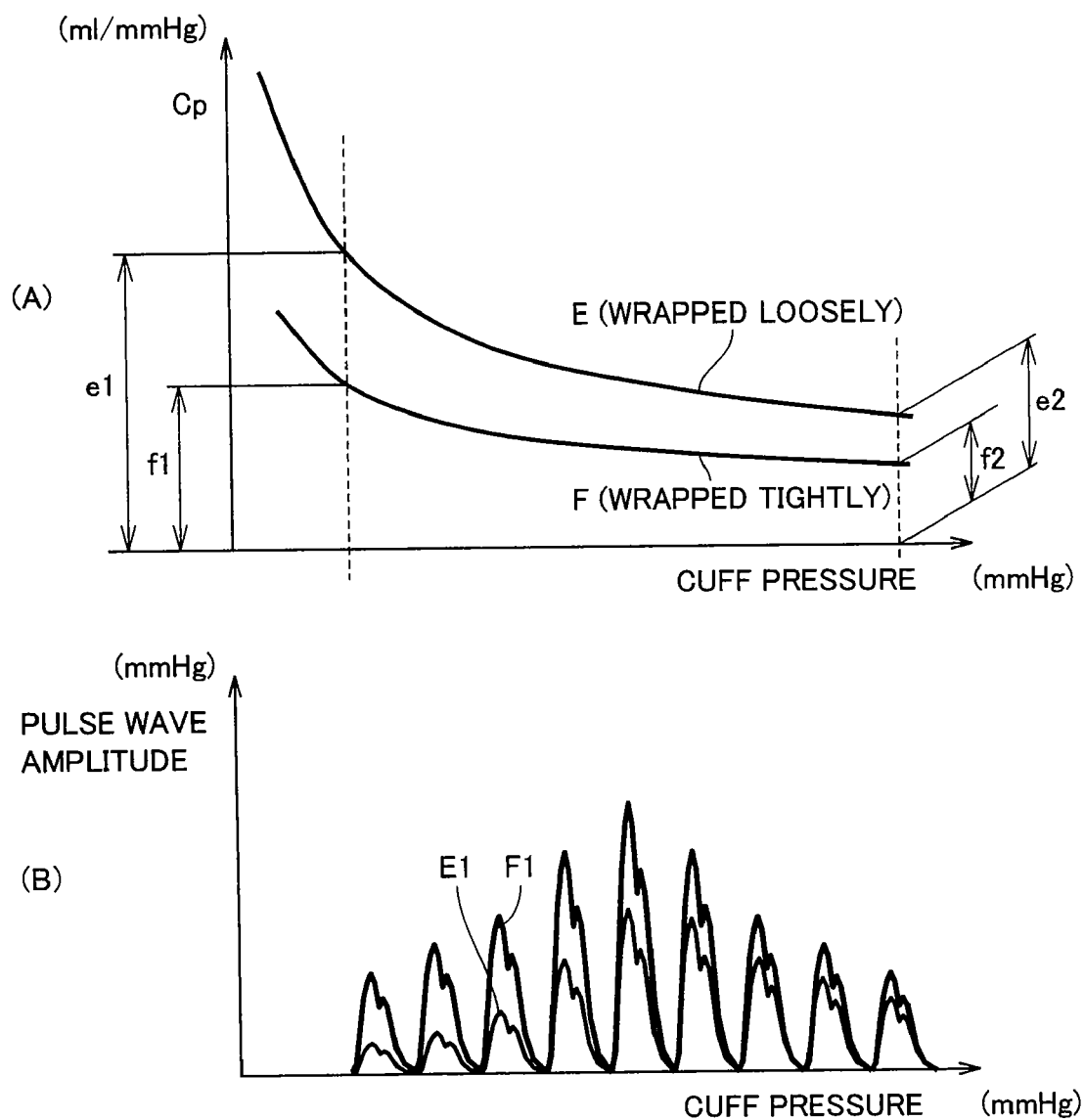
FIG.17 WHEN WRAPPING STATE DIFFERS

ELECTRONIC BLOOD PRESSURE MEASUREMENT DEVICE CALCULATING BLOOD PRESSURE VALUE

TECHNICAL FIELD

The present invention relates to an electronic blood pressure measurement device for measuring blood pressure by pressing a measurement site such as the upper arm of a living body with a bladder, particularly to an electronic blood pressure measurement device for calculating a blood pressure value according to change in internal pressure in the bladder that occurs based on volumetric change of the blood vessel pressed through the bladder.

BACKGROUND ART

Conventionally, an electronic blood pressure measurement device employing the oscillometric method is provided. At this electronic blood pressure measurement device, the internal pressure in a bladder located in a cuff (hereinafter, referred to as cuff pressure) wrapped around a measurement site identified as a portion of a living body is adjusted for calculation of a blood pressure value according to change in internal pressure in the bladder that occurs based on volumetric change of the blood vessel that is pressed at the measurement site (hereinafter, referred to as pressure pulse wave). In such an electronic blood pressure measurement device, it is important that the volumetric change of the blood vessel is accurately reflected as the cuff pressure changes. The bladder has a predetermined maximum volume, and is formed of a stretchable resin material that allows variable volume in a range that does not exceed the maximum volume as air is introduced/discharged.

When the cuff pressure (mmHg) changes during blood pressure measurement, the volumetric change of the blood vessel with respect to the pulsatory motion also changes. In an electronic blood pressure measurement device employing the oscillometric method, the volumetric change of the blood vessel is detected as a pressure pulse wave overlapping with the cuff pressure. The systolic and diastolic blood pressure values are calculated based on the pulse wave envelope formed by the detected pressure pulse waves (a curve formed of a collection of pressure pulse waves). The calculating procedure of the blood pressure and pulse count based on the pulse wave envelope is well known, and details thereof will not be presented here.

During blood pressure measurement, it is desirable that the change in the cuff pressure properly reflects the volumetric change of the artery. Variation in the conveyance sensitivity of the volumetric change of the artery corresponding to the cuff pressure will cause reduction in the accuracy of the blood pressure measurement. In other words, variation in the state of the cuff (how tight the cuff is wrapped around the measurement site (namely, the volume of the bladder), or the circumferential length of the arm at the measurement site where the cuff is wrapped, the softness of the measurement site, and the like) will lead to variation in the level of the pressure change obtained corresponding to the blood pressure volumetric change with respect to the same level.

Cuff compliance (ml/mmHg) is known as one index that can express this conveyance sensitivity. The cuff compliance ($Cp=dV/dP$) is an index representing the cuff volumetric change (dV) to the cuff pressure change (dP). The conveyance sensitivity becomes lower as cuff compliance Cp becomes higher. In other words, the level of pressure change to volumetric change of the same level becomes smaller as the cuff compliance becomes larger.

FIG. 14 schematically shows the relationship of cuff compliance Cp and the amplitude (mmHg) of the pulse wave signal with respect to the change in cuff pressure. Relationship (A) of FIG. 14 represents the change in cuff compliance Cp to the change in cuff pressure. A straight line segment A corresponds to the case where the rate of cuff volumetric change according to change in the cuff pressure is constant, i.e. the value of cuff compliance Cp is constant (parallel) to the change in cuff pressure. When air is input to or output from the bladder of the cuff, the cuff compliance will change and not become constant to the cuff pressure, as indicated by curve B, different from line segment A, even if the same cuff pressure change is presented.

In relationship (B) of FIG. 14, the change in the amplitude of the pulse wave signal detected concurrently is designated as A1 and B1, when a cuff having a bladder corresponding to the detection of cuff compliance Cp of line segment A and curve B in relationship (A) is wrapped around a measurement site (upper arm). The pulse wave amplitude detected when cuff compliance Cp is constant with respect to the cuff pressure (line segment A) is designated A1. The pulse wave detected when cuff compliance Cp varies with respect to the cuff pressure (curve B), i.e. when the volumetric change rate of the bladder of the cuff is not constant, is designated B1.

The pulse wave amplitude represents the volumetric change of the blood vessel pressed by the cuff. In the case where the blood vessel volumetric change is conveyed without lost via the cuff and detected by a pressure sensor or the like, the blood pressure can be measured accurately. However, when cuff compliance Cp varies with respect to the cuff pressure as in curve B, the detected pulse wave amplitude indicating the pulse wave component will be distorted due to the variation. Therefore, distortion occurs in the pulse wave envelope corresponding to a series of such pulse wave signals.

Distortion of the pulse wave amplitude is exhibited such that the amplitude is increased at the high level side of the cuff pressure and reduced at the low level side of the cuff pressure, respectively. A high cuff pressure means that the bladder is sufficiently inflated by the great amount of air introduced therein. Therefore, the amplitude of the pressure pulse wave indicating the volumetric change of the blood vessel pressed by the cuff is distorted to become larger than the pressure pulse wave amplitude indicating the actual volumetric change value of the blood vessel. In contrast, when the cuff pressure is low, the amount of air in the bladder is low. Therefore, the pressure pulse wave amplitude indicating the volumetric change of the blood vessel pressed by such a cuff is distorted to become smaller. Thus, the blood pressure measurement accuracy is degraded by the distortion component set forth above in the event of air being input to and output from the bladder, as in curve B.

FIG. 15 represents the relationship of cuff compliance Cp and the pulse wave amplitude according to cuff pressure change when the cuff is wrapped around a measurement site (upper arm), corresponding to the arm size at the measurement site (length around the arm). In relationship (A) of FIG. 15, the relationship between cuff compliance Cp and the pulse wave amplitude is represented by curves A and B corresponding to the case where the circumferential length of the arm is long and short, respectively.

In relationship (B) of FIG. 15, the pulse wave amplitude change detected when the cuff pressure change is as in relationship (A) is indicated by a pulse wave signal designated A1 and a pulse wave signal designated B1. The pulse wave signal of A1 corresponds to the case where cuff compliance Cp changes as in curve A. The pulse wave signal of B1 corresponds to the case where cuff compliance Cp changes as in curve B. As indicated in the drawings, since the volume of the bladder in the wrapped cuff is larger for the longer circumferential length than for the shorter circumferential length, the volumetric change (volumetric change rate) in the bladder required to achieve a predetermined cuff pressure will be larger for the longer circumferential length than for the shorter circumferential length, resulting in a detected pulse wave amplitude smaller for the longer circumferential length than for the shorter circumferential length.

In addition, the ratio of cuff compliance Cp differs between the high side and low side of the cuff pressure, depending upon the arm thickness. In other words, cuff compliance Cp ratio b2/b1 of the high pressure side to the low pressure side at a small arm size of curve B differs from cuff compliance Cp ratio a2/a1 for a large arm size of curve A. Therefore, the detected pulse wave amplitude is greatly distorted depending upon the arm thickness.

FIG. 16 represents the relationship of cuff compliance Cp and the pulse wave amplitude according to cuff pressure change when the cuff is wrapped around a measurement site (upper arm), corresponding to the softness of the arm (soft/firm) at the measurement site. In relationship (A) of FIG. 16, the relationship between cuff compliance Cp and the pulse wave amplitude is represented by curve C and curve D corresponding to a soft arm and a firm arm, respectively.

In relationship (B) of FIG. 16, the pulse wave amplitude change detected when the cuff pressure change is as in relationship (A) is indicated by a pulse wave signal designated C1 and a pulse wave signal designated D1. The pulse wave signal of C1 corresponds to the case where cuff compliance Cp changes as in curve C. The pulse wave signal of D1 corresponds to the case where cuff compliance Cp changes as in curve D. As indicated in the drawings, the required air volume of the cuff to achieve the same cuff pressure will be larger if the measurement site (arm) is soft than if the arm is firm, resulting in a detected pulse wave amplitude smaller for the soft arm than for the firm arm. In addition, the ratio of cuff compliance Cp differs between the high side and low side of the cuff pressure, depending upon the softness of the arm. In other words, cuff compliance Cp ratio d2/d1 of the high pressure side to the low pressure side at a firm arm of curve D differs from cuff compliance Cp ratio c2/c1 for a soft arm of curve C. Therefore, the detected pulse wave amplitude is greatly distorted depending on the arm softness.

Thus, the different cuff compliance ratio between a soft arm and a firm arm according to the cuff pressure will cause the pressure pulse wave amplitude to be distorted. Therefore, the accuracy of the blood pressure measurement will vary depending upon the soft/firm arm.

FIG. 17 represents the relationship of cuff compliance Cp and the pulse wave amplitude according to cuff pressure change when the cuff is wrapped around a measurement site (upper arm), corresponding to the wrapping tightness of the cuff at the measurement site. In relationship (A) of FIG. 17, the relationship between cuff compliance Cp and the pulse wave amplitude is represented by curve E and curve F corresponding to a tightly wrapped case and loosely wrapped case, respectively.

In relationship (B) of FIG. 17, the pulse wave amplitude change detected when the cuff pressure change is as in relationship (A) of FIG. 17 is indicated by a pulse wave signal designated E1 and a pulse wave signal designated F1. The pulse wave signal of E1 corresponds to the case where cuff compliance Cp changes as in curve E. The pulse wave signal of F1 corresponds to the case where cuff compliance Cp changes as in curve F.

As appreciated from the drawing, in the case where the cuff is wrapped loosely around the measurement site, an amount of air that allows blood pressure measurement, even if introduced sufficiently into the bladder of the cuff, will need to be further increased in the bladder to actually press the cuff against the measurement site. This means that the amount of air volume to be introduced into the cuff bladder is increased as compared to the case where the cuff is wrapped tightly in order to raise the cuff pressure to the same level. Thus, the amount of air to be introduced in the cuff bladder in order to raise the cuff pressure to the same level is increased in the state where the cuff is wrapped loosely as compared to the state where the cuff is wrapped tightly or appropriately. Thus, the detected pressure pulse wave amplitude becomes smaller in a loosely wrapped state as compared to the tightly or appropriately wrapped state even if the cuff pressure is the same.

In contrast, when the cuff is wrapped tightly, the required amount of air to be introduced into the bladder in order to raise the cuff pressure to the same level is smaller as compared to a loosely wrapped state. Therefore, the detected pressure pulse wave is larger than in a loosely wrapped state. Thus, the level of the pulse wave amplitude differs as indicated by E1 and F1 in relationship (B) of FIG. 17 even if the cuff pressure is the same, depending upon the state of wrapping tightness (wrapped tightly or loosely) around the measurement site. Similarly as described above, cuff compliance Cp ratio differs between the high side and low side of the cuff pressure, depending upon the wrapping state. Cuff compliance Cp ratio e2/e1 of the high pressure side to the low pressure side differs from cuff compliance Cp ratio f2/f1 in a tightly wrapped state of curve F, so that the pulse wave is distorted due to the cuff volumetric change ratio not being constant (refer to relationship (A) of FIG. 17). Thus, the accuracy of blood pressure measurement will be degraded due to the wrapping state.

As shown in FIGS. 14-17, change occurs in the pulse wave amplitude corresponding to the volumetric change of the blood pressure when the cuff state (softness of arm, circumferential length of arm, cuff wrapping tightness) changes. Moreover, the pulse wave amplitude will change if cuff compliance Cp differs. Thus, even if the artery is squeezed with the same cuff pressure, the detected pulse wave amplitude will vary, i.e. be distorted, depending upon the cuff state and difference in cuff compliance Cp.

Conventional approaches of blood pressure measurement taking into account the cuff state and compliance are disclosed in patent documents.

Japanese Patent Laying-Open No. 5-329113 discloses the method of measurement including the steps of identifying in advance the cuff volumetric change property with respect to the cuff pressure, converting a signal of the cuff pressure change to volumetric change, and correcting the blood pressure value using the same for measurement. In accordance with this method, the cuff pressure and volumetric change property must be prepared in advance.

Japanese Patent Laying-Open Nos. 11-309119 and 11-318835 disclose a sphygmomanometer cuff including pressing means for supplying a predetermined amount of fluid to a fluid bladder for squeezing the human body to press the fluid bladder against the living body.

Japanese Patent Laying-Open No. 5-269089 discloses a sphygmomanometer cuff including a small inner cuff into which a conductive liquid of low viscosity is introduced for pressing against an artery, configured to press the inner cuff against a human body using an outer cuff located at the outer side of the inner cuff.

Patent Document 1: Japanese Patent Laying-Open No. 5-329113
Patent Document 2: Japanese Patent Laying-Open No. 11-309119
Patent Document 3: Japanese Patent Laying-Open No. 11-318835
Patent Document 4: Japanese Patent Laying-Open No. 5-269089

DISCLOSURE OF THE INVENTION

Problems to be Solved by the Invention

The changing properties employed in Japanese Patent Laying-Open No. 5-329113 vary infinitely corresponding to how the cuff is wrapped, the thickness and softness of the arm, and the like. It was therefore difficult to conduct sufficient correction.

In addition, a plurality of complicated procedures for the correction (detecting the flow rate differing for each measurement, detecting the arm size, detecting the wrapping state, detecting the softness of the human body, and the like) is required, involving a large-scale device. It is not appropriate for practical usage.

The methods of Japanese Patent Laying-Open Nos. 11-309119 and 11-318835 are involved in change in the volume with respect to the pressure, caused when the fluid bladder of a constant volume is pressed against the human body. The volumetric change is increased as the pressure becomes lower, causing reduction and increase in the amplitude of the detected pressure pulse wave via the fluid bladder as the pressure becomes lower and higher, respectively. The volume ratio to the pressure is particularly increased when the fluid bladder for detecting the pressure pulse wave is small. The pressure pulse wave is readily distorted, so that the blood pressure cannot be measured properly.

The method of Japanese Patent Laying-Open No. 5-269089 is characterized in that a conductive liquid of low viscosity that is non-contractible is introduced into the inner cuff that squeezes against the artery, pressing the human body with another outer cuff from the outer side. Although the fluid volume in the inner cuff is always constant irrespective of change in the fluid pressure to allow pressing at a constant volume, the pressure pulse wave is apt to become dull due to the poor conductance of the blood vessel volumetric change by the fluid, leading to degradation in accuracy. There is also the problem that the fluid sealed in the inner cuff readily leaks.

In view of the foregoing, an object of the present invention is to provide an electronic blood pressure measurement device of high measurement accuracy, suppressing the influence of change in compliance (cuff volumetric change to cuff pressure change) on the pulse wave component.

Means for Solving the Problems

According to an aspect of the present invention, an electronic blood pressure measurement device includes a measurement bladder having a predetermined amount of air sealed to press against a measurement site, a pressure detection portion detecting a pressure signal of an internal pressure in the measurement bladder, a pulse wave detection portion detecting a pulse wave amplitude included in the pressure signal detected by the pressure detection portion, a squeezing portion exerting externally applied pressure to the measurement bladder to press against the measurement site by the measurement bladder, and a blood pressure calculation portion.

Information of cuff compliance property obtained from the change in internal pressure and volume of the measurement bladder in which a predetermined amount of air is sealed is stored in advance. The blood pressure calculation portion includes a pulse wave amplitude detection portion detecting a pulse wave amplitude by the pulse wave detection portion in a process of changing the internal pressure in the measurement bladder by changing the externally applied pressure to the measurement bladder through the squeezing portion, and a correction portion correcting the pulse wave amplitude detected by the pulse wave amplitude detection portion using the information of cuff compliance property stored in advance. The blood pressure is calculated based on the pulse wave amplitude corrected by the correction portion.

Preferably, the correction portion includes a first correction portion correcting the information of cuff compliance property stored in advance to indicate constant cuff compliance to change in internal pressure. The pulse wave amplitude detected by the pulse wave amplitude detection portion is corrected by the first correction portion according to the amount of correction of the information of cuff compliance property stored in advance.

Preferably, the correction portion corrects the pulse wave amplitude detected at an internal pressure lower than and higher than the internal pressure indicated by the pressure signal detected by the pressure detection portion when a peak of the pulse wave amplitude is detected by the pulse wave amplitude detection portion to become larger and smaller, respectively.

Preferably, the cuff compliance property includes a volumetric change with respect to change in internal pressure approximating a straight line with a gentle slope.

Preferably, the squeezing portion includes a pressing-securing air bag provided at an outer circumference of the blood pressure measurement bladder pressing against a measurement site, having an internal diameter reduced or extended by inflation or deflation to change externally applied pressure towards the measurement bladder.

Preferably, the squeezing portion includes a band member provided at the outer circumference of the blood pressure measurement bladder that presses against the measurement site. The tension on the band member is adjusted to reduce or extend the inner diameter of the band member to change the externally applied pressure to the measurement bladder.

Effects of the Invention

The present invention is based on a configuration in which a measurement bladder having a predetermined amount of air always sealed, i.e. having a predetermined volume, is squeezed by the squeezing portion at the measurement site. Accordingly, the volumetric change with respect to change in internal pressure indicated by the cuff compliance property of the measurement bladder is substantially constant (not readily altered), independent of the measurement state (softness of the measurement site, size in association with wrapping the measurement bladder around the measurement site, way of wrapping the measurement bladder, and the like). By changing the externally applied pressure to the measurement bladder in which a predetermined amount of air is sealed without drawing in/out air during blood pressure measurement, the amplitude of the pressure pulse wave detected at the measurement site by the pulse wave detection portion is corrected based on the obtained cuff compliance property.

By this correction, the inclusion of artifacts other than blood pressure information (volumetric change of measurement bladder) caused by the difference in the wrapping way of the measurement bladder around the measurement site (tightly wrapped/loosely wrapped), the size in association with the wrapping around the measurement site, softness of the measurement site, and the like, into the pulse wave amplitude can be avoided, allowing more accurate calculation of the blood pressure.

BRIEF DESCRIPTION OF THE DRAWINGS

FIG. 1 is a blood pressure measurement flowchart according to a first embodiment.

FIG. 4 schematically represents an appearance of the electronic blood pressure measurement device of the first embodiment and a state of usage for blood pressure measurement.

FIG. 15 represents the relationship of cuff compliance and pulse wave amplitude in accordance with change in cuff pressure, corresponding to the arm size.

FIG. 17 represents the relationship of cuff compliance and pulse wave amplitude in accordance with change in cuff pressure, corresponding to the level of the cuff wrapping tightness.

Figure 2:
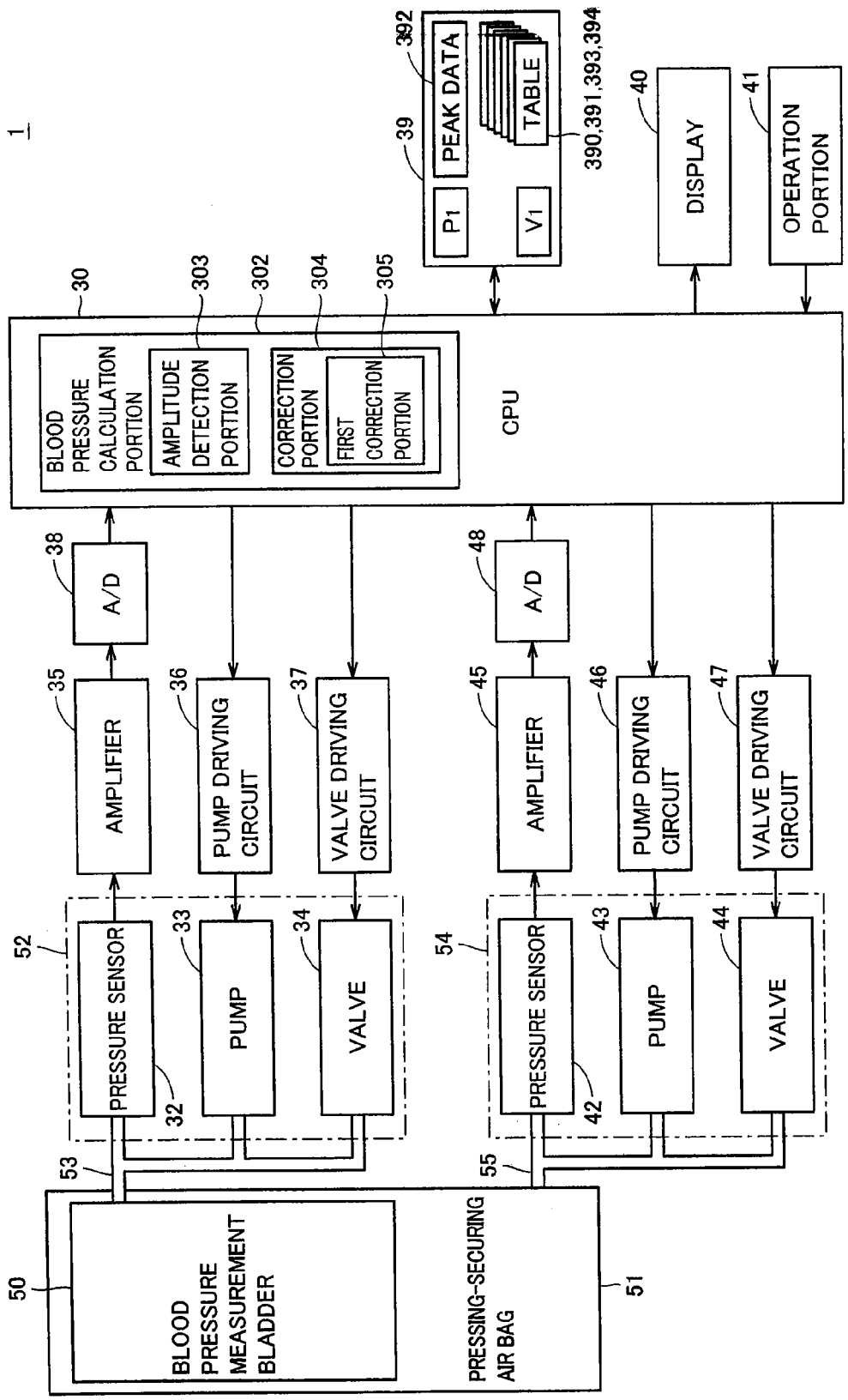
FIG. 2 is a block diagram of an electronic blood pressure measurement device of the first embodiment.

DESCRIPTION OF THE REFERENCE CHARACTERS 1, 2 electronic blood pressure measurement device; 50 blood pressure measurement bladder; 51 pressing-securing air bag; 95 squeeze fixture portion; 97 reel squeeze portion

BEST MODES FOR CARRYING OUT THE INVENTION

Embodiments of the present invention will be described hereinafter with reference to the drawings. It is assumed that the electronic blood pressure measurement device of the present embodiments employs the blood pressure measurement method according to the oscillometric method.

In each embodiment, the P-V property representing the relationship of pressure-volume will not easily change, independent of the measurement state (softness of measurement site, size of measurement site, wrapping way, and the like), by wrapping and squeezing a bladder of a predetermined volume around a measurement site of the human body at the time of blood pressure measurement. By referring to the cuff compliance property obtained in advance from the P-V property for usage in correction during blood pressure calculation, the accuracy of blood pressure measurement can be improved.

Although it is assumed that the upper arm is taken as the measurement site in each embodiment, the measurement site is not limited to the upper arm, and may be another site such as the wrist.

In addition, the electronic blood pressure measurement device according to each embodiment employs the type that automatically wraps an arm cuff in which a bladder is incorporated around the measurement site. The automatic wrapping type includes, but not limited to, the type having the wrapping diameter of the blood pressure measurement bladder around a measurement site reduced by inflation of the pressing-securing air bag by means of a curler, as shown in the first embodiment, and the type having the tension of the arm band increased to reduce the wrapping diameter of the arm band around the measurement site through motor rotation, as in the second embodiment that will be described afterwards.

First Embodiment

Figure 3:
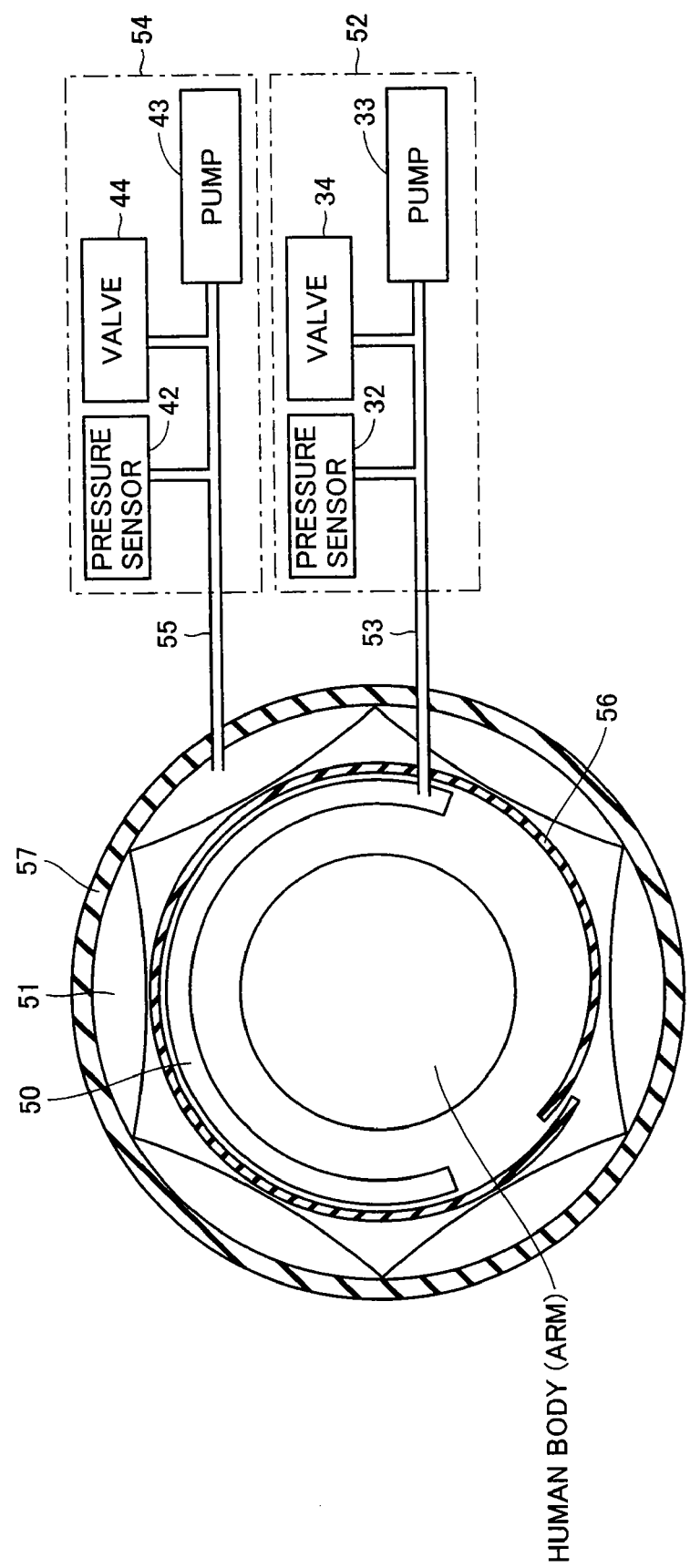
FIG. 3 represents the air system of the electronic blood pressure measurement device of the first embodiment.

FIG. 1 represents a blood pressure measurement flow chart according to the first embodiment. FIG. 2 represents a block configuration of the electronic blood pressure measurement device of the first embodiment; FIG. 3 represents the air system of the electronic blood pressure measurement device of the first embodiment; and FIG. 4 schematically shows an appearance of the electronic blood pressure measurement device of the first embodiment and a state of usage for blood pressure measurement.

(Device Configuration)

Referring to FIG. 2, an electronic blood pressure measurement device 1 includes a blood pressure measurement bladder 50, a pressing-securing air bag 51, a blood measurement air system 52 to supply or discharge air to or from blood pressure measurement bladder 50 via a tube (air tube) 53, an amplifier 35, a pump driving circuit 36, a valve driving circuit 37, and an A/D (Analog/Digital) converter 38, provided in association with blood pressure measurement air system 52. Electronic blood pressure measurement device 1 further includes a squeezing air system 54 to supply or discharge air to or from pressing-securing air bag 51 via a tube 55, an amplifier 45, a pump driving circuit 46, a valve driving circuit 47, and an A/D converter 48, provided in association with squeezing air system 54. Electronic blood pressure measurement device 1 further includes a CPU (Central Processing Unit) 30 to control and monitor each element in a centralized manner, a memory 39 to store various information such as a program to cause a predetermined operation by CPU 30, the measured blood pressure value and the like, a display 40 to display various information including the blood pressure measurement result, and an operation portion 41 operated to enter various designations for measurement.

CPU 30 functions as a blood pressure calculation portion 302 to calculate blood pressure based on measurement data. Blood pressure calculation portion 302 includes an amplitude detection portion 302 detecting the amplitude of a pulse wave, and a correction portion 304 correcting the detected pulse wave amplitude. Correction portion 304 includes a first correction portion 305 correcting the cuff compliance property.

The function of blood pressure calculation portion 302 is implemented by execution of a corresponding program read out from memory 39 by CPU 30.

Blood pressure measurement air system 52 includes a pressure sensor 32 detecting and providing pressure (hereinafter, referred to as cuff pressure P) in pressure measurement bladder 50, a pump 33 to supply air to blood pressure measurement bladder 50, and a valve 34 opened/closed to discharge or seal in air in blood pressure measurement bladder 50. Amplifier 35 amplifies an output signal of pressure sensor 32 and provides the amplified output signal to A/D converter 38. A/D converter 38 converts the applied analog signal into a digital signal for output to CPU 30. Pump driving circuit 36 controls the drive of pump 33 based on a control signal applied from CPU 30. Valve driving circuit 37 effects open/closure control of valve 34 based on a control signal applied from CPU 30.

Squeezing air system 54 includes a pressure sensor 42 to detect pressure in pressing-securing air bag 51 for output, a pump 43 to supply air to pressing-securing air bag 51, and a valve 44 opened/closed to discharge or seal in air from or to pressing-securing air bag 51. Amplifier 45 amplifies an output signal from pressure sensor 42 for output to A/D converter 48. A/D converter 48 converts an applied analog signal into a digital signal for output to CPU 30. Pump driving circuit 46 controls the drive of pump 43 according to a control signal applied from CPU 30. Valve driving circuit 47 controls the open/closure of valve 44 according to a control signal applied from CPU 30.

Referring to FIG. 4 (A), electronic blood pressure measurement device 1 includes a cylindrical case 57 to secure the upper arm that is the measurement site of a subject, and a blood pressure measuring device main portion 58. Blood pressure measurement device main portion 58 includes an LCD 59 and a lamp 60 for display 40. Blood pressure measurement device main portion 58 includes a power switch 61, as well as a start switch 62 and a stop switch 63 to designate the start and stop of blood pressure measurement, as operation portion 41 to allow externally applied operation. Blood pressure measurement bladder 50 that is to be attached to the measurement site is provided at the inner circumferential face of cylindrical case 57. FIG. 4 (B) represents the state where the upper arm that is the measurement site of the subject is inserted for blood pressure measurement from the front direction of the drawing of cylindrical case 57.

FIG. 3 schematically represents a transverse sectional view of cylindrical case 57 in the state of usage of FIG. 4 (B). Cylindrical case 57 has, from the outer circumferential side of the upper arm that is the measurement site towards the inner circumferential face of cylindrical case 57, blood pressure measurement bladder 50, squeezing curler 56 substantially of a cylindrical shape and of flexible member, deforming in the radical direction of the inner diameter of the arm that is the measurement site, and pressing-securing air bag 51 located therein. When air is gradually supplied by squeezing air system 54 to cause inflation of pressing-securing air bag 51, the diameter of squeezing curler 56 is reduced thereby. In response, blood pressure measurement bladder 50 located between squeezing curler 56 and the human body (upper arm) is pressed against the measurement site. Accordingly, blood pressure measurement bladder 50 is wrapped around the human body (arm) by squeezing curler 56 and pressing-securing air bag 51, allowing blood pressure measurement.

Pressing-securing air bag 51 and blood pressure measurement bladder 50 are formed of resin material such as flexible polyvinyl chloride, EVA (ethylene-vinyl acetate copolymer), PU (polyurethane) and the like, capable of stretching (volumetric change) by the discharge or supply of air. Squeezing curler 56 is formed of a flexible resin material superior in restorability such as PP (polypropylene), PE (polyethylene), and the like.

(Blood Pressure Measurement Procedure)

In FIG. 1, (A) and (B) represent flow charts for blood pressure measurement according to the present embodiment. The program according to the flowchart is prestored in memory 39. Blood pressure measurement is effected by CPU 30 reading out this program from memory 39 and executing the program.

According to the procedures in (A) and (B) of FIG. 1, when a subject to be measured inserts his/her arm as shown in FIG. 4(B) to start measurement, initialization is first carried out (step ST1). A predetermined amount of air is supplied to blood pressure measurement bladder 50 to set the cuff volume of blood pressure measurement bladder 50 to a predetermined level (step ST2). Then, air is supplied to pressing-securing air bag 51 to gradually increase the internal pressure (step ST3). In response, the wrapping diameter of squeezing curler 56 is reduced by inflation of pressing-securing air bag 51. Blood pressure measurement bladder 50 begins to exert pressure on the measurement site. When cuff pressure P of blood pressure measurement bladder 50 pressed against the measurement site of the body by air supply to pressing-securing air bag 51 arrives at a predetermined level, the air in pressing-securing air bag 51 is discharged so that the internal pressure in pressing-securing air bag 51 is gradually reduced (step ST4). During this pressure reducing process, blood pressure calculation (step ST5) of FIG. 1(B) is carried out by blood pressure calculation portion 302. The blood pressure measurement result is stored in memory 39 and displayed at display 40 (step ST6). The air in pressing-securing air bag 51 and blood pressure measurement bladder 50 is discharged rapidly until the internal pressure in both bladders correspond to the level of atmospheric pressure. Thus, the measurement ends (ST7).

At step ST5, CPU 30 inputs a detection signal of the cuff pressure to extract (sampling) a component of the pressure pulse wave overlapping with the input cuff pressure signal. When sampling of a plurality of pressure pulse waves (pulse wave signal) allowing formation of a pulse wave envelope ends, the produced pulse wave envelope is corrected using a correction coefficient obtained in advance, and blood pressure measurement (calculation) is carried out based on the corrected pulse wave envelope.

The blood pressure measurement set forth above is directed to, but not limited to, a reducing pressure measurement method for calculating blood pressure during the process of gradually reducing the internal pressure in pressing-securing air bag 51. For example, the blood pressure measurement may be directed to an increasing pressure measurement method for calculating blood pressure during the process of gradually increasing the internal pressure in pressing-securing air bag 51 for pressurization at step ST3. Similarly in the increasing pressure measurement mode, a pulse wave envelope is formed and corrected using a correction coefficient obtained in advance to carry out blood pressure measurement (calculation) based on the corrected pulse wave envelope. The processes of (A) and (B) of FIG. 1 will be described in detail.

(Process of Step ST1)

In the state of FIG. 4(B), the subject operates start switch 62 of electronic blood pressure measurement device 1 to turn on the power, whereby electronic blood pressure measurement device 1 is initialized. In the initialization, valves 34 and 44 are completely opened through valve driving circuits 37 and 47 to completely discharge air from blood pressure measurement bladder 50 and pressing-securing air bag 51. Accordingly, the internal pressure in blood pressure measurement bladder 50 and pressing-securing air bag 51 is equivalent to the atmospheric pressure. In addition, CPU 30 adjusts the output of pressure sensors 52 and 54 to correspond to 0 mmHg.

(Process of Step ST2)

Figure 5:
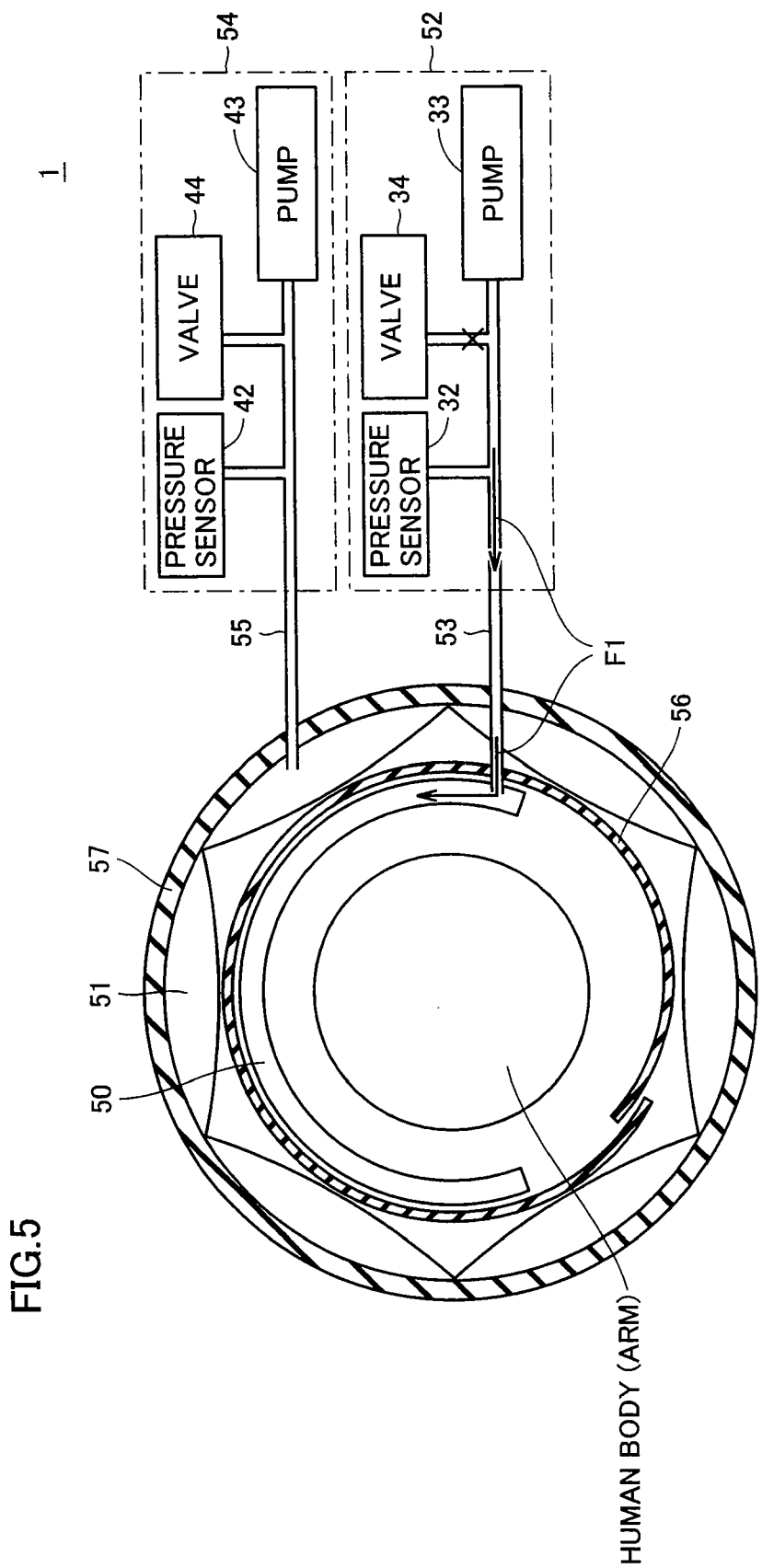
FIG. 5 schematically represents an example of adjustment of the air system during blood pressure measurement according to the first embodiment.

In the present process, CPU 30 controls valve driving circuit 37 such that valve 34 of blood pressure measurement air system 52 is closed, as shown in FIG. 5. It is to be noted that valve 44 of squeezing air system 54 is open. Then, CPU 30 controls pump driving circuit 36 to drive pump 33, whereby a predetermined amount of air is fed into blood pressure measurement bladder 50 in the direction of arrow 'F1'. Then, pump 33 is stopped to cease air delivery to blood pressure measurement bladder 50. Blood pressure measurement bladder 50 wrapped around the measurement site in the state not having externally applied pressure by pressing-securing air bag 51 attains a sealed state after a predetermined amount of air is delivered.

The predetermined amount of air to be fed to blood pressure measurement bladder 50 can be controlled by attaching a flow monitor and identifying the flow rate. However, this method requires a complicated configuration. Therefore, CPU 30 may define the predetermined flow rate based on a predetermined voltage and driving time during the control of pump driving circuit 36 to drive pump 33. Since data defining the predetermined voltage and driving time for a predetermined flow rate is prestored in memory 39, CPU 30 reads out the relevant data from memory 39 and controls pump driving circuit 36 based on the data read out. Accordingly, air of a predetermined flow rate is fed to blood pressure measurement bladder 50 by pump 33.

(Process of Step ST3)

Blood pressure measurement is initiated with a predetermined amount of air sealed in blood pressure measurement bladder 50, as shown in FIG. 5. The volume of blood pressure measurement bladder 50 inflated with a predetermined amount of air is the initial volume $V_1$. The data of initial volume $V_1$ is empirically obtained in advance and stored in memory 39, and read out for usage. The cuff pressure in blood pressure measurement bladder 50 (referred to as initial cuff pressure $P_1$) at this initial volume is detected by pressure sensor 32 and stored in memory 39.

Figure 6:
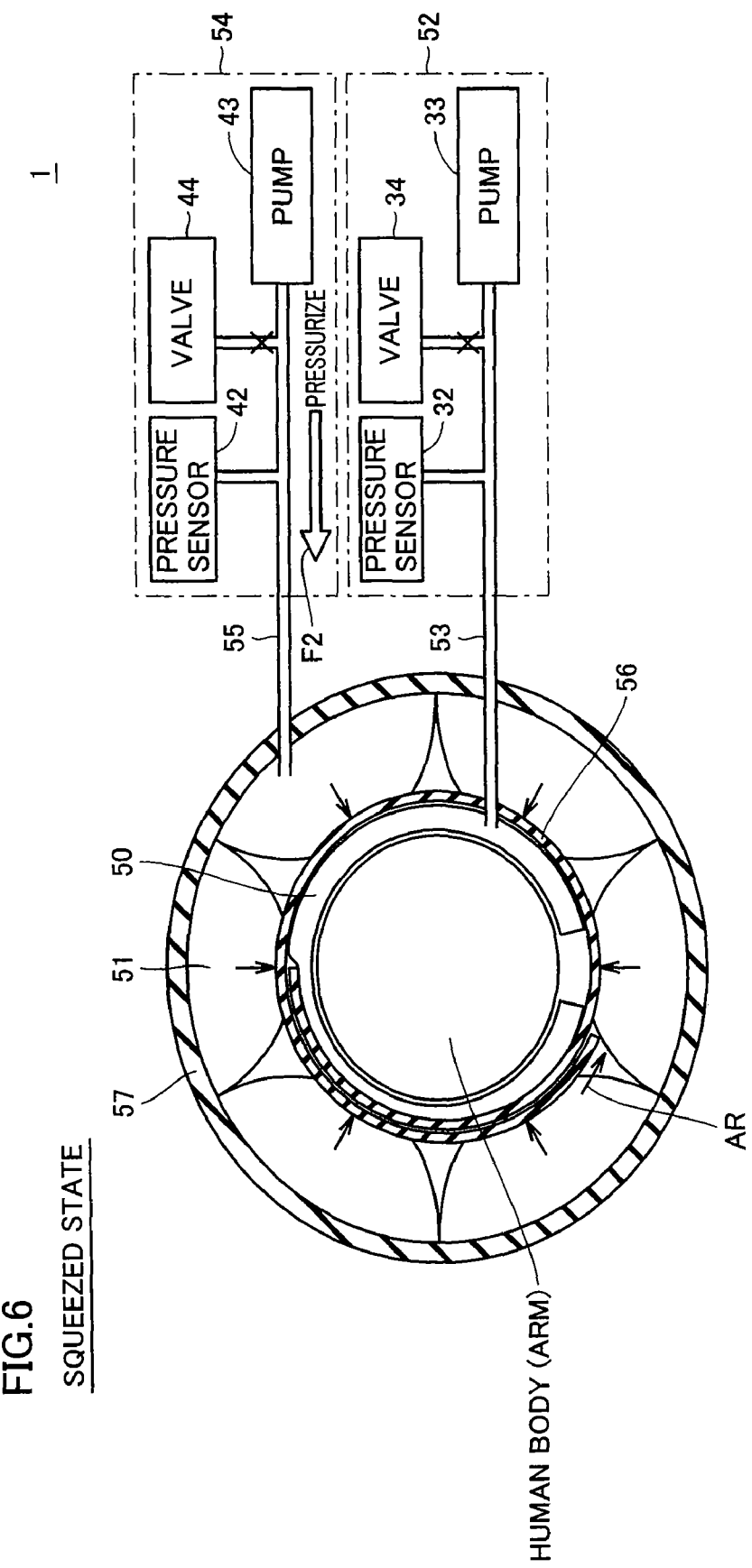
FIG. 6 schematically represents another example of adjustment of the air system during blood pressure measurement according to the first embodiment.

Then, CPU 30 controls valve driving circuit 47 such that valve 44 of squeezing air system 54 is closed, as shown in FIG. 6. Then, CPU 30 controls pump driving circuit 46 to drive pump 43, whereby air is gradually introduced to pressing-securing air bag 51 in the direction of arrow 'F2' in the drawing. Accordingly, pressing-securing air bag 51 is gradually inflated. By this inflation, the end of squeezing curler 56 moves towards the direction of arrow 'AR'. As a result, the diameter of squeezing curler 56 is reduced. In response, blood pressure measurement bladder 50 located between squeezing curler 56 and the measurement site is pressed against the measurement site. Pump 43 is continuously driven thereafter to cause continuation of inflation of pressing-securing air bag 51. The exerted pressure towards the measurement site by blood pressure measurement bladder 50 continues to rise.

During this rising process of the exerted pressure, the cuff pressure identified by the internal pressure in blood pressure measurement bladder 50 is detected by pressure sensor 32 of blood pressure measurement air system 52. A signal indicating the detected cuff pressure is provided to CPU 30 via amplifier 35 and A/D converter 38. This sequentially detected cuff pressure is taken as cuff pressure $P_2$. When detection is made that cuff pressure $P_2$ indicated by the applied cuff pressure signal has risen to a predetermined pressure level, CPU 30 controls pump drive circuit 46 such that pump 43 is stopped. Accordingly, the delivery of air to pressing-securing air bag 51 by pump 43 ceases.

(Process of Step ST4)

Figure 7:
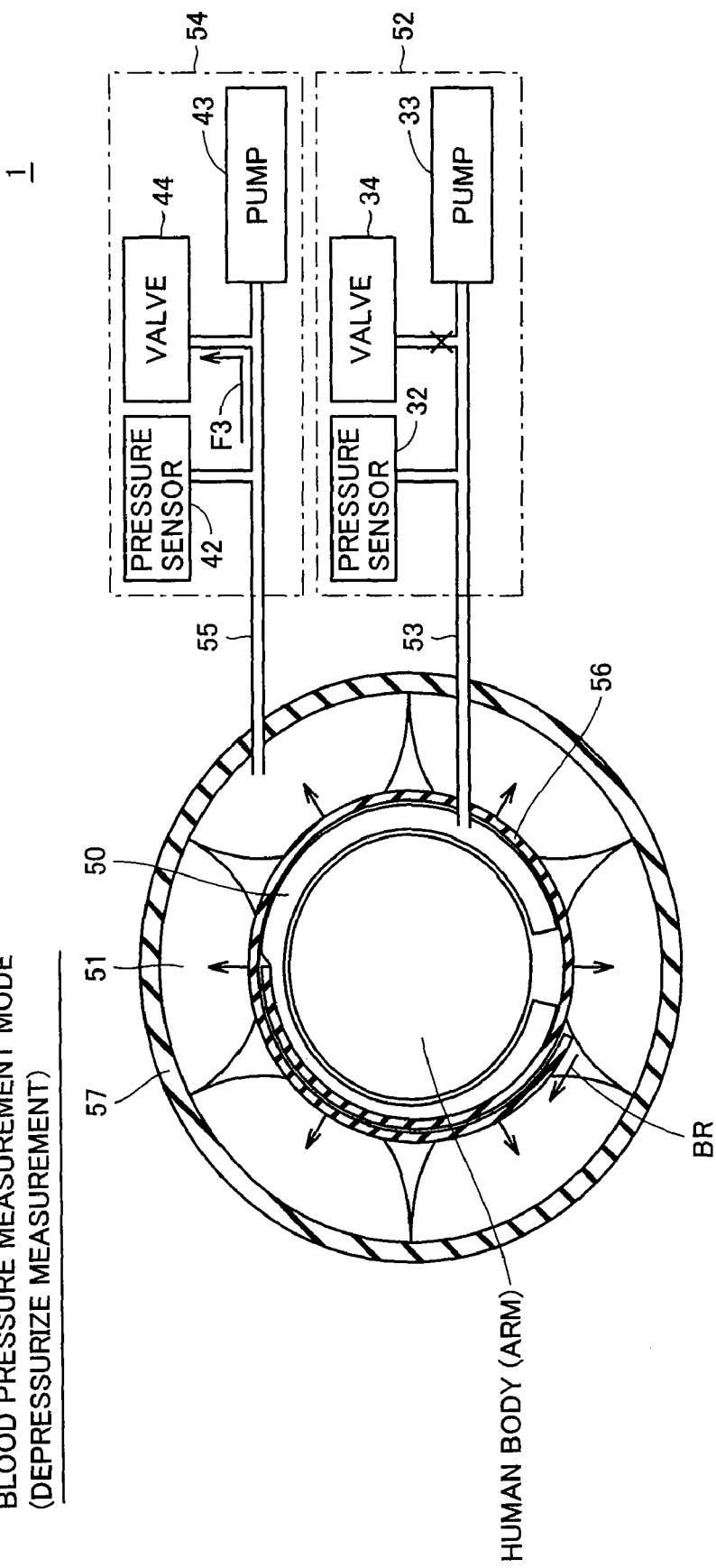
FIG. 7 schematically represents a further example of adjustment of the air system during blood pressure measurement according to the first embodiment.
Figure 8:
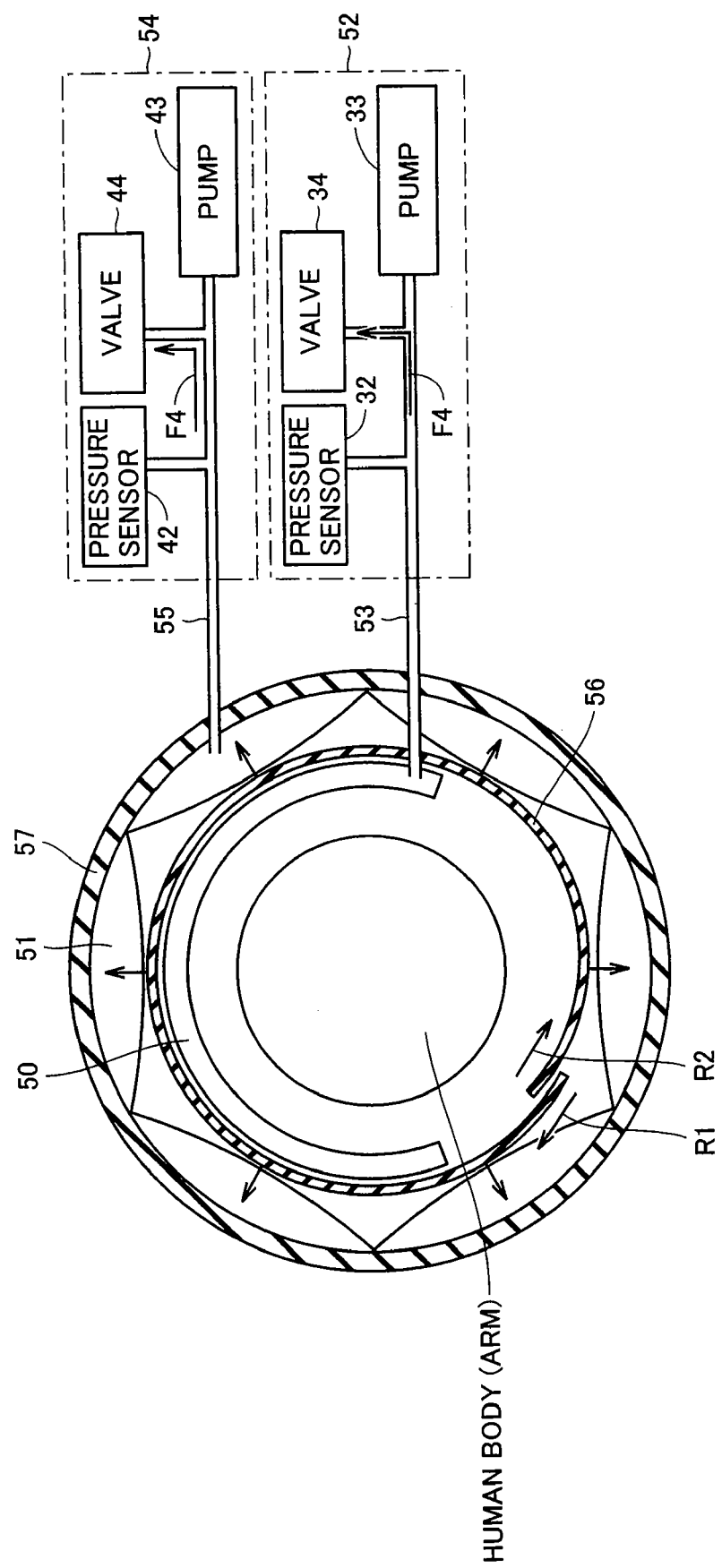
FIG. 8 schematically represents still another example of adjustment of the air system during blood pressure measurement according to the first embodiment.

When the cuff pressure arrives at a predetermined level and the drive of pump 43 is ceased, valve driving circuit 47 is controlled such that valve 44 of squeezing air system 54 gradually opens as shown in FIG. 7. The air in pressing-securing air bag 51 is gradually discharged in the direction of arrow 'F3' (extremely slow discharge). In response, the end of squeezing curler 56 is shifted in the direction of arrow 'BR', so that the diameter of squeezing curler 56 increases. According to this increasing diameter, the exerted pressure on the measurement site by blood pressure measurement bladder 50 located between squeezing curler 56 and the measurement site is reduced. Since the pressure applied on the blood pressure measurement site is gradually reduced, the pressure pulse wave indicating the volumetric change of the blood vessel at the measurement site overlaps with the cuff pressure signal detected by pressure sensor 32 of blood pressure measurement air system 52. The cuff pressure signal detected by pressure sensor 32 is applied to CPU 30 via amplifier 35 and A/D converter 38. CPU 30 carries out blood pressure measurement (blood pressure calculation) of step ST5 during the reducing pressure process according to the procedure of (B) in FIG. 1.

(Process of Step ST5)

CPU 30 inputs the cuff pressure signal applied from pressure sensor 32, and samples a pulse wave signal indicating the overlapping pressure pulse wave (ST10, ST13). Specifically, amplitude detection portion 303 detects the amplitude level of the pulse wave signal included in the cuff pressure signal, and stores the detected amplitude level in correspondence with the cuff pressure level indicated by the cuff pressure signal detected at that point of time in a table 391 in memory 39. Every time an amplitude level and cuff pressure level are stored in table 391, CPU 30 detects the peak value of the pulse wave envelope (step ST15). In other words, when the amplitude level of the current sampled pulse wave signal is larger than the amplitude level of the last detected pulse wave signal, the amplitude level of the current sampled pulse wave signal is stored in association with the level of the corresponding cuff pressure signal in memory 39 as peak data 392 (peak data 392 is updated). In contrast, when the amplitude level of the current sampled pulse wave signal is not larger than the amplitude level of the last detected pulse wave signal, peak data 392 is not updated. Therefore, the data corresponding to peak data 392 will indicate the peak value of the relevant pulse wave envelope at the point of time when the data for forming a pulse wave envelope is stored in table 391.

When detection is made that CPU 30 has finished sampling a predetermined number of pulse wave signals required for formation of a pulse wave envelope, i.e. when determination is made that the peak value of the relevant pulse wave envelope has been determined (YES at step ST17), control proceeds to step ST19 that will be described afterwards. When determination is made that the peak value has not yet been determined (NO at step ST17), control returns to step ST10, and a sampling process is repeated thereafter in a manner similar to that set forth above.

When CPU 30 determines that the peak value has been defined, i.e. when determination is made that the storage of data for forming a pressure pulse wave envelope in table 391 has been completed (YES at step ST17), correction portion 304 carries out the process to calculate the coefficient required to correct the pulse wave envelope (step ST19), as will be described afterwards. Then, correction portion 304 corrects the produced pulse wave envelope using the correction coefficient, i.e. corrects the data in table 391 (step ST21). Then, blood pressure calculation portion 302 determines the parameter of blood pressure calculation based on the data of the corrected pulse wave envelope in table 391, i.e. calculates the systolic blood pressure and diastolic blood pressure based on the well known procedure (step ST23).

(Process of Step ST6)

CPU 30 stores the calculated result of step ST5 in memory 39, and displays the result on display 40.

(Process of Step ST7)

When the process of step ST6 ends, CPU 30 controls respective elements such that valve 34 of blood pressure measurement air system 52 and valve 44 of squeezing air system 52 and valve 44 of squeezing air system 54 are completely open. Accordingly, air is rapidly discharged from blood pressure measurement bladder 50 and pressing-securing air bag 51 in the direction of arrow 'F4' in the drawing. This discharge causes shrinkage of pressing-securing air bag 51, whereby the end of squeezing curler 56 shifts in the direction of arrows 'R1' and 'R2'. As a result, the diameter of squeezing curler 56 is altered to return to the former size. According to this change in diameter, the exerted pressure on the measurement site by blood pressure measurement bladder 50 located between squeezing curler 56 and the measurement site is reduced, and eventually becomes zero. By this procedure of discharge, the internal pressure in blood pressure measurement bladder 50 and pressing-securing air bag 51 is reduced to eventually correspond to the atmospheric pressure. Thus, blood pressure measurement ends.

(Calculation of Correction Coefficient)

The procedure of calculating a correction coefficient according to the present embodiment in step ST 19 will be described with reference to FIGS. 9 and 10. First, the principle of the measurement scheme employing a bladder of a predetermined volume (predetermined volume bladder measurement scheme) will be described.

<Predetermined Volume Bladder Measurement Scheme>

Figure 9:
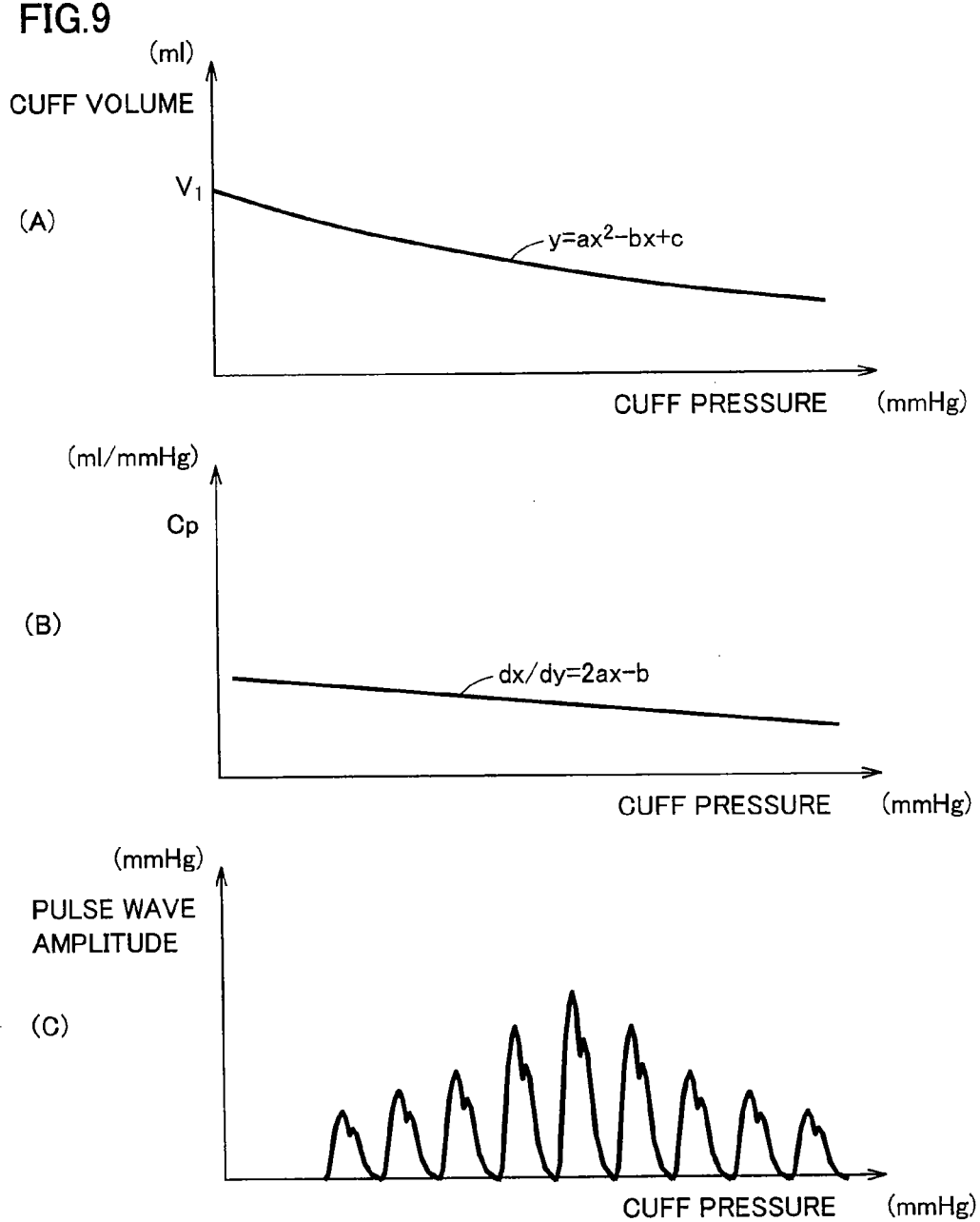
FIG. 9 is a diagram to describe a predetermined volume bladder measurement scheme according to the first embodiment.

The predetermined volume bladder measurement scheme according to the present invention is represented in (A)-(C) of FIG. 9.

A cuff of a material, size and structure similar to those of blood pressure measurement bladder 50 is prepared. The cuff has a predetermined amount of air sealed therein. When that cuff is pressed against a human body, the relationship between the internal pressure and volume of the cuff will change. This relationship is represented by equation 1 set forth above under the state change of ideal gas.

[Equation 1]

$$P_1 V_1^\kappa = P_2 V_2^\kappa \qquad (1)$$

($P_1$: initial cuff pressure; $V_1$: initial volume; $P_2$: cuff pressure when pressed; $V_2$: cuff volume: $\kappa$ adiabatic index)

Using $V_1$ for the initial volume, cuff volume $V_2$ can be obtained by equation 2 set forth below. The condition of equation 2 corresponds to the case where there is no heat exchange between the gas in the cuff and the environment, and no internal heat caused by friction or the like.

[Equation 2]

Let $P_1$=atmospheric pressure(760 mmHg), then $P_2$=
$(760+P_2) V_2 = (760/(760+P_2) \times V_1^\kappa)^{1/\kappa}$ (2)

Figure 16:
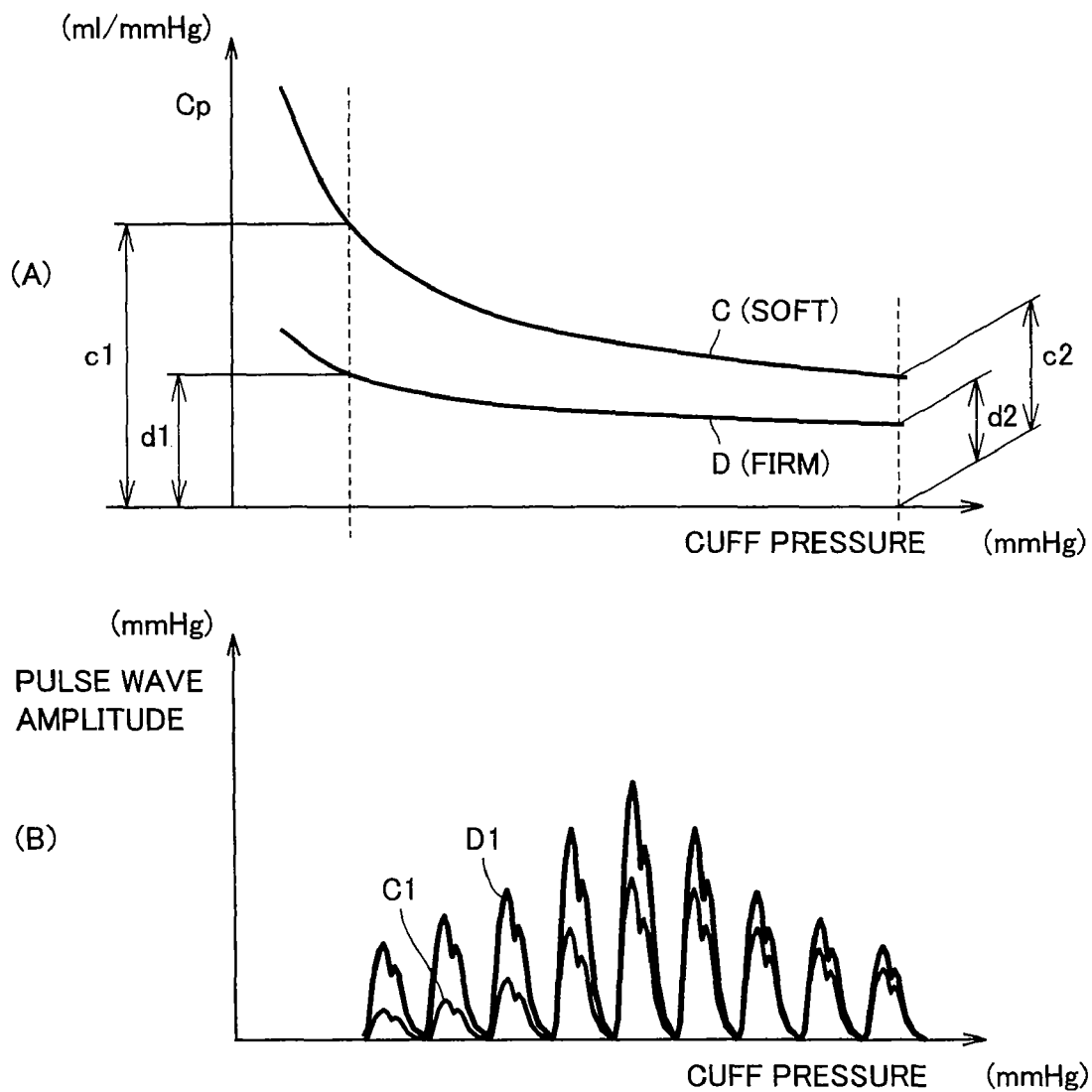
FIG. 16 represents the relationship of cuff compliance and pulse wave amplitude in accordance with change in cuff pressure, corresponding to the softness of the arm.

Since the volume and pressure in the cuff is altered by urging a cuff (blood pressure measurement bladder 50) with a predetermined volume against the human body, i.e. air is not externally input/output with respect to the cuff (blood pressure measurement bladder 50), cuff compliance Cp obtained from the relationship between cuff pressure and volume will substantially not change, as compared to the conventional scheme (FIGS. 15, 16 and 17), even if the arm size, softness, and wrapping state differ. Specifically, the relationship as shown in (A) of FIG. 9 is obtained. (A) of FIG. 9 has the cuff volume (ml) plotted along the vertical axis and the cuff internal pressure (cuff pressure) plotted along the horizontal axis. As appreciated from the drawing, the relationship between the cuff pressure and volume (P-V property) is always constant, and indicated using the equation of $y=ax^2-bx+c$ (where y=cuff volume and x=cuff pressure).

Cuff compliance Cp used herein can be calculated by differentiating the equation representing the relationship between the cuff pressure and cuff volume shown in (A) of FIG. 9. Therefore, the relationship between cuff compliance Cp and the cuff pressure is represented by the equation of the line segment in (B) of FIG. 9. This relevant line segment equation is represented as $(dx/dy=2ax-b)$. It is appreciated that cuff compliance Cp approximates a straight line even if the cuff pressure changes.

Thus, the cuff volumetric change corresponding to change in cuff pressure when blood pressure measurement is carried out using a cuff of a predetermined volume indicating the property of (A) and (B) in FIG. 9 is suppressed more than by the method of drawing in/out air with respect to the cuff, independent of the arm size, softness, and wrapping tightness. Moreover, the change in the obtained cuff compliance Cp is approximated to a straight line having a gentle slope. Therefore, serious distortion of the amplitude of a pulse wave signal overlapping the cuff pressure caused by cuff pressure change can be suppressed (refer to (C) in FIG. 9).

Under such state where air is not drawn in/out with respect to blood pressure measurement bladder 50 of a predetermined volume, the amplitude of a pulse wave conveying the volumetric change of the blood vessel at the site where the cuff compliance is to be measured can be detected accurately. As a result, the accuracy of blood pressure calculation using a pulse wave envelope formed from pulse wave amplitudes is improved.

<Correction of Cuff Compliance>

The correction method of further improving the accuracy using blood pressure measurement bladder 50 of a predetermined volume will be described hereinafter. A predetermined coefficient is used for correction.

Determination of a correction coefficient in actual blood pressure measurement using a bladder of a predetermined volume shown in (A)-(C) of FIG. 9 will be described with reference to (A) and (B) of FIG. 10. (A) of FIG. 10 represents cuff compliance Cp (ml/mmHg) indicating the cuff volumetric change rate corresponding change in the cuff pressure (mmHg) plotted along the horizontal axis.

In the foregoing measuring scheme using a bladder of predetermined volume, the cuff compliance property corresponding to change in cuff pressure is designated by a straight line having a constant gentle slope, even if the measurement state (arm thickness, arm softness, and cuff wrapping tightness) differs. A correction coefficient is obtained taking advantage of this property.

Required data are obtained by experiments prior to blood pressure measurement (at the time of factory shipment) and stored in a table in memory 39. Specifically, a predetermined amount of air is introduced into blood pressure measurement bladder 50, and then blood pressure measurement bladder 50 is sealed. The sealed blood pressure measurement bladder 50 is wrapped around the measurement site of a subject to be measured or a dummy body, and externally applied pressure is exerted on the measurement site. Under this squeezed state, the data of P-V property shown in (A) of FIG. 9 are obtained by actual readings. The P-V property data obtained by actual readings is stored in table 390 of memory 39. Data representing the property of cuff compliance-cuff pressure in (B) of FIG. 9 is calculated based on the data in table 390. The calculated data is stored in table 393 in memory 39.

Figure 10:
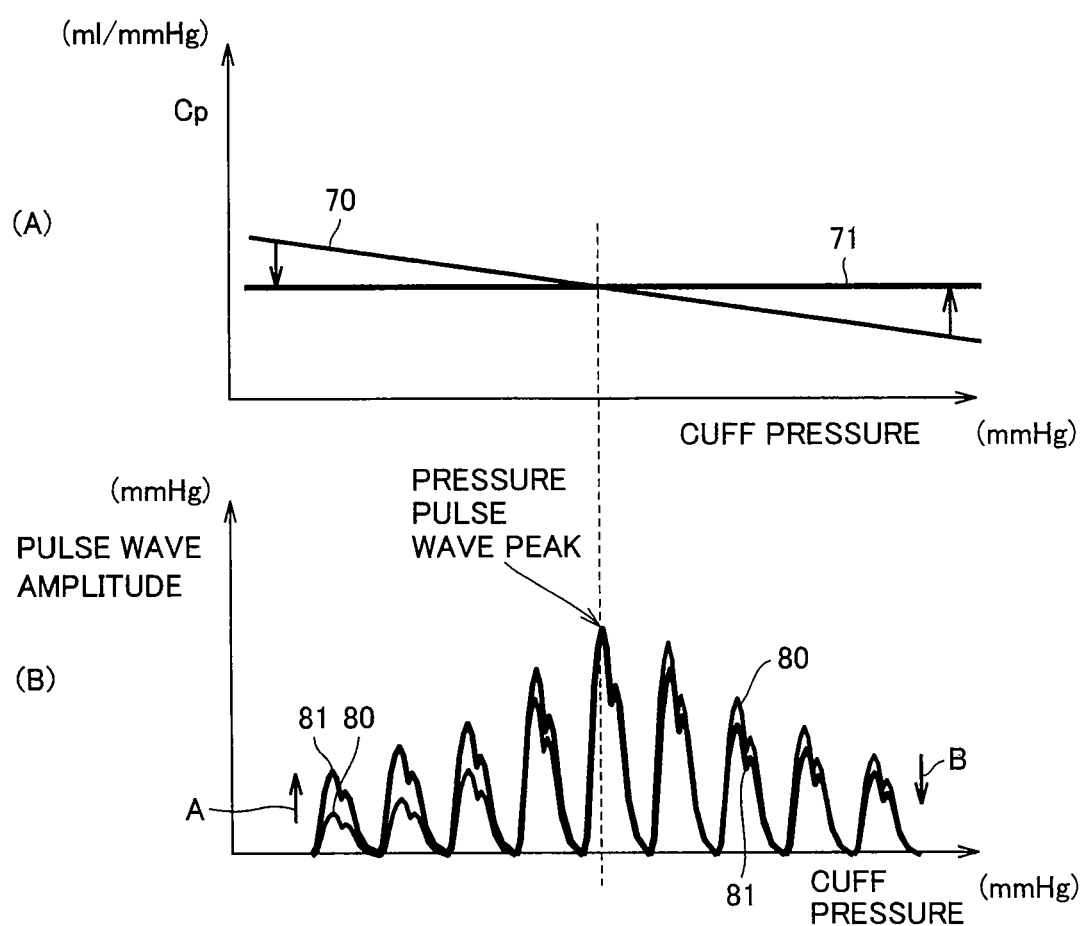
FIG. 10 is a diagram to describe a predetermined volume bladder measurement correction method according to the first embodiment.

Based on the foregoing measurement resultant data obtained in advance, first correction portion 305 calculates at step ST19 a correction coefficient such that cuff compliance Cp is constant, irrespective of change in cuff pressure, as shown in Fig. (A) of FIG. 10. Specifically, CPU 30 reads out data from table 393 that indicates the actually measured cuff compliance-cuff pressure property. Accordingly, data of straight line 70 in (A) of FIG. 10 is read out. Then, peak data 392 of the pulse wave amplitude is read out from memory 39. Based on straight line 70 data and peak data 392 read out, the data of a straight line 71 (refer to (A) of FIG. 10) representing the cuff compliance-cuff pressure property having no change in cuff compliance Cp with respect to cuff pressure is calculated. Straight line 71 is a straight line passing through a predetermined cuff compliance Cp designated by straight line 70 (this refers to cuff compliance Cp corresponding to the cuff pressure at the point of time when peak data 392 is detected), and indicating the property of no change in cuff compliance Cp even if the cuff pressure changes. In other words, straight line 71 is assumed to be a straight line parallel to the axis of the cuff pressure, as indicated in (A) of FIG. 10.

Then, first correction portion 305 carries out processing to set the data of straight line 70 to coincide with the data of straight line 71. Specifically, correction is made such that cuff compliance Cp is reduced and increased at the side lower than and higher than the cuff pressure, respectively, indicated by peak data 392, with respect to the data of straight line 70. Accordingly, the value of cuff compliance Cp indicated by straight line 70 is corrected (added or subtracted) in the direction of the arrows in FIG. 10(A). According to the corrected amount, correction portion 304 corrects the data of the pulse wave envelope (pulse wave amplitude) in table 391 detected during the reducing pressure process. As used herein, the value of cuff compliance Cp indicated by straight line 70 in (A) of FIG. 10 is called the correction coefficient of the correction amount for matching with the value of straight line 71. In the present embodiment, it is assumed that the data of a correction coefficient corresponding to each cuff pressure indicated by peak data 392 that can be expected is calculated in advance and stored in table 394 of memory 39.

In the present embodiment, the method set forth below is applied to correction. Using a bladder of a material, size, and structure similar to those of blood pressure measurement bladder 50 actually mounted on electronic blood pressure measurement device 1, the P-V property is obtained prior to blood pressure measurement. The cuff compliance Cp-cuff pressure property is calculated based on the obtained P-V property, and a correction coefficient is calculated using the calculated cuff compliance Cp-cuff pressure property. The data of the calculated correction coefficient is stored as table 394 in memory 39. It is to be noted that the applied method is not limited thereto. For example, the data of the cuff compliance Cp-cuff pressure property may be prestored in table 393 (in memory 39), and CPU 30 may calculate the correction coefficient each time blood pressure measurement is to be carried out based on peak data 392 and data in table 393 read out from memory 39.

The procedure of obtaining a correction coefficient may be based on prestoring a correction coefficient in memory 39 as the information of the property of cuff compliance Cp, or based on directly storing the property per se of cuff compliance Cp in memory 39 and cause CPU 30 to calculate a correction coefficient every time blood pressure is measured. In other words, the information of the property of cuff compliance Cp includes, but not limited to, such correction coefficient and cuff compliance Cp property per se.

(Correction of Pulse Wave Envelope)

Correction of a pulse wave envelope by correction portion 304 using the information of cuff compliance property will be described hereinafter.

Referring to FIG. 10(B), correction of the pulse wave envelope is carried out according to the correction coefficient of cuff compliance Cp corresponding to the information of the cuff compliance property in (A) of FIG. 10. In (B) of FIG. 10, the data stored in pulse wave envelope table 391 is designated by the relationship between the cuff pressure and the pulse wave amplitude designated by reference number 80. As used herein, the relationship of reference number 80 is corrected to correspond to the relationship between the cuff pressure and the pulse wave amplitude designated by reference number 81. Namely, the data in pulse wave envelope table 391 is corrected.

Specifically, with regards to the cuff pressure data in pulse wave envelope table 391, the pulse wave amplitude data corresponding to cuff pressure data representing a level lower than the cuff pressure indicated by peak data 392 is corrected such that the amplitude is increased, as indicated by reference number 81 (refer to arrow A), using the correction coefficient in table 394. This is because, at the side lower than the cuff pressure indicated by peak data 392, cuff compliance Cp indicating the cuff volumetric change according to a cuff pressure change of a predetermined amount becomes larger in proportion to a lower cuff pressure. Pulse wave amplitude data corresponding to cuff pressure data representing a level higher than the cuff pressure indicated by peak data 392 is corrected such that the amplitude is reduced, as indicated by reference number 81 (refer to arrow B), using the correction coefficient of table 394. This is because, at the side higher than the cuff pressure indicated by peak data 392, the cuff volumetric change according to a cuff pressure change of a predetermined amount becomes smaller in proportion to a higher cuff pressure. Thus, the amount of correction of the pulse wave amplitude corresponding to a certain cuff pressure depends upon the degree of difference between the cuff compliance detected according to the certain cuff pressure and the cuff compliance detected according to the cuff pressure when the peak of the pulse wave amplitude was detected, i.e. depends on the value of the correction coefficient. The amount of correction of the pulse wave amplitude corresponding to a certain cuff pressure can be determined using the correction coefficient. In other words, according to the difference and slope of cuff compliance Cp obtained based on straight line 71 indicating that cuff compliance Cp is constant at the relevant cuff pressure and straight line 70 indicating that cuff compliance Cp changes gently (straight line 70 with a gentle slope), CPU 30 conducts calculation using a predetermined calculating formula to determine the amount of correction.

The cuff pressure corresponding to the peak value of the pulse wave amplitude indicated by peak data 392 substantially corresponds to the mean blood pressure. At step ST23, blood pressure calculation portion 302 calculates the systolic blood pressure and the diastolic blood pressure by the well-known calculation algorithm from the corrected pulse wave amplitude waveform.

Second Embodiment

The previous first embodiment employs a pressing-securing air bag 51 for wrapping blood pressure measurement bladder 50 around the measurement site. Alternatively, the tension of a belt may be employed as in the second embodiment, instead of the inflation/deflation of pressing-securing air bag 51.

Figure 11:
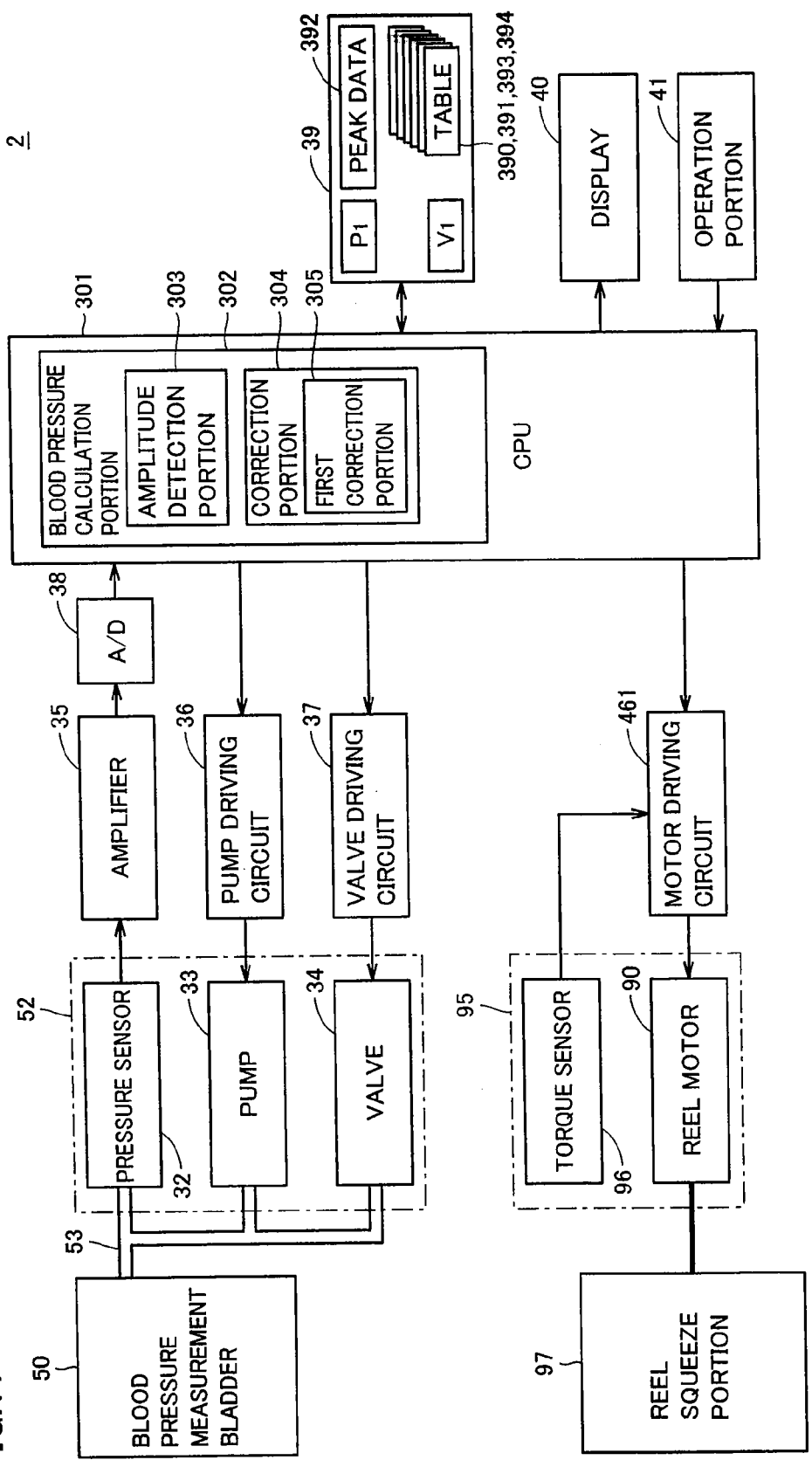
FIG. 11 is a block diagram of an electronic blood pressure measurement device according to a second embodiment.
Figure 12:
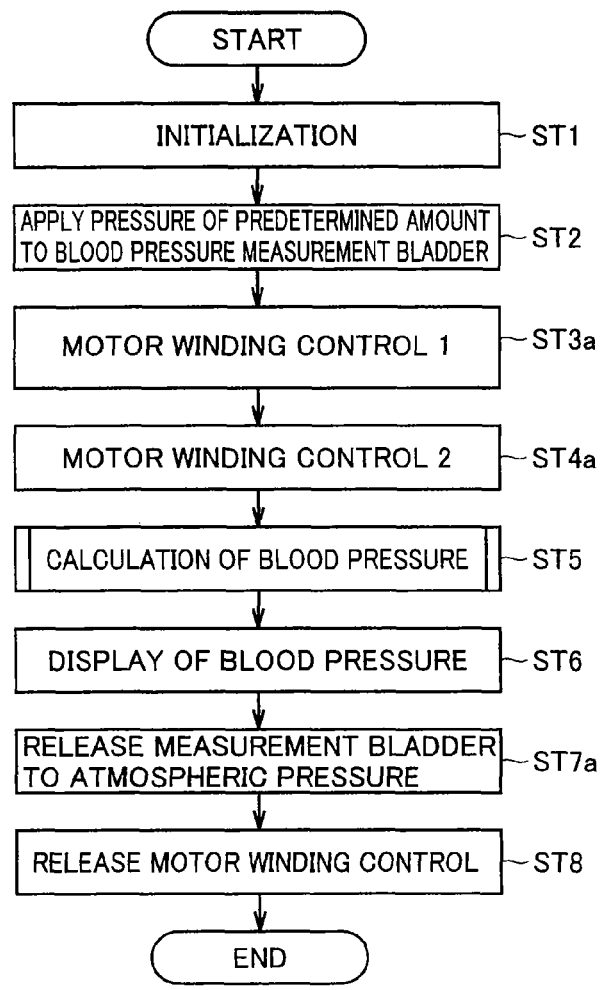
FIG. 12 is a blood pressure measurement flow chart according to the second embodiment.
Figure 13:
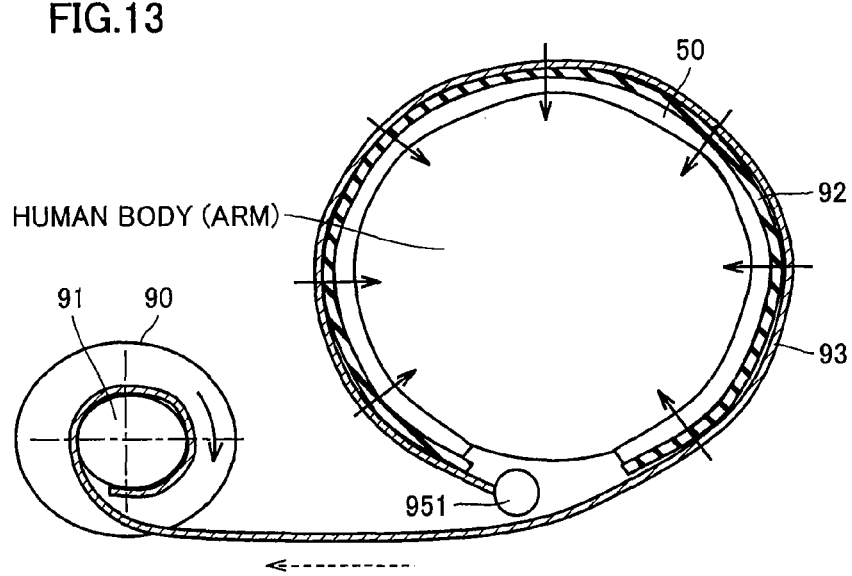
FIG. 13 represents the air system together with the wrapping function of the electronic blood pressure measurement device of second embodiment.
Figure 14:
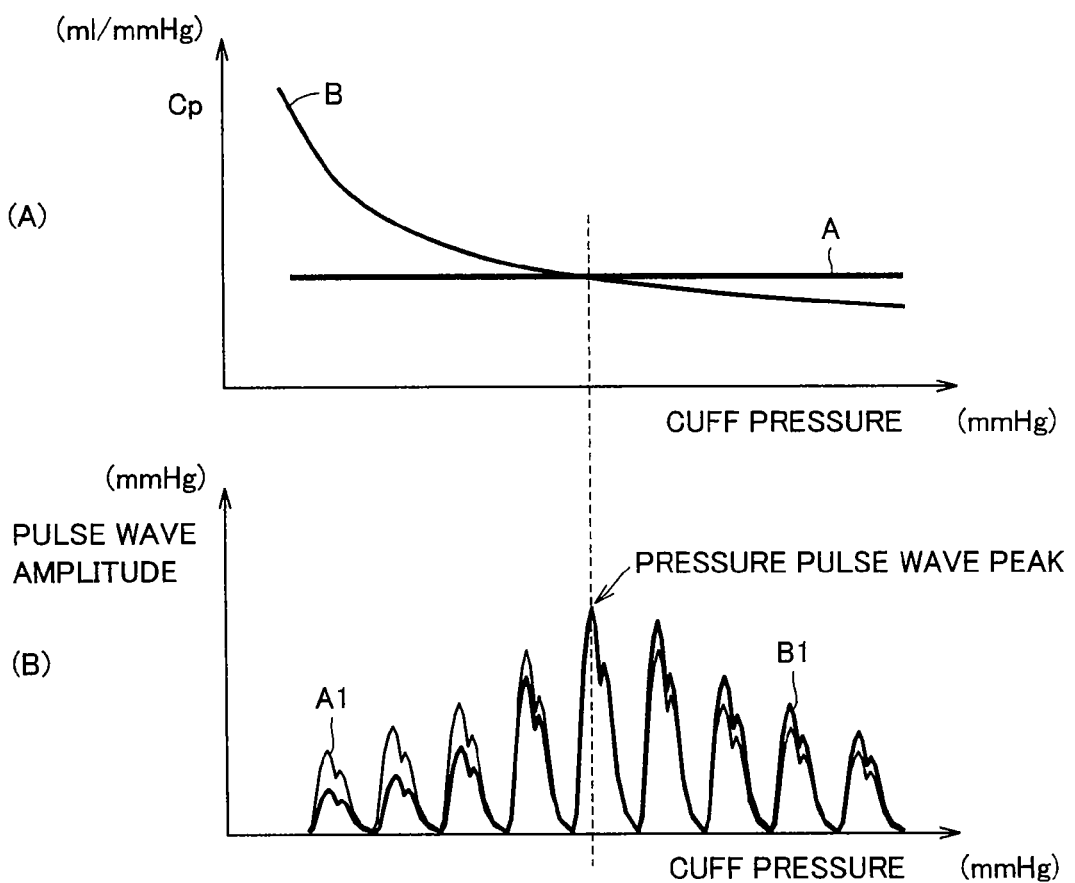
FIG. 14 schematically represents the relationship of cuff compliance and pulse wave amplitude corresponding to change in cuff pressure.

The functional configuration of an electronic blood pressure measurement device 2 of the second embodiment is shown in FIG. 11. The process flow chart of blood pressure measurement is shown in FIG. 12. The wrapping structure is schematically shown in FIG. 13. Referring to these figures, the difference between electronic blood pressure measurement device 2 of FIG. 11 and electronic blood pressure measurement device 1 of FIG. 2 is set forth below. Specifically, electronic blood pressure measurement device 2 includes a reel squeeze portion 97 instead of pressing-securing air bag 51 of FIG. 2, a CPU 301 instead of CPU 30, as well as a squeeze fixture portion 95 and a motor driving circuit 461 instead of squeezing air system 54, amplifier 45, pump driving circuit 46, valve driving circuit 47, and A/D converter 48. The remaining elements of electronic blood pressure measurement device 2 are identical to those of electronic blood pressure measurement device 1 of FIG. 2. Reel squeeze portion 97 functions likewise with pressing-securing air bag 51. Squeeze fixture portion 95 is connected to reel squeeze portion 97 via a cable.

Squeeze fixture portion 95 functions to wind blood pressure measurement bladder 50 around the measurement site (upper arm) via reel squeeze portion 97 formed of a belt 93 and a curler 92. Squeeze fixture portion 95 includes a reel motor 90 and a torque sensor 96 detecting the reeling ability thereof. The detected result of torque sensor 96 is applied to a motor driving circuit 461. Motor driving circuit 461 has its drive controlled by CPU 301. Motor driving circuit 461 rotates reel motor 90 based on the detected result from torque sensor 96 when ON (driven) by CPU 301. One end of a band-like belt 93 formed of a flexible material is wound around a reel 91 of reel motor 90. The other end of belt 93 is affixed at an anchorage point 951. Electronic blood pressure measurement device 2 includes blood pressure measurement bladder 50 corresponding to an inner cylindrical face through which the upper arm region is inserted, and a cylindrical curler 92 formed of flexible resin material of favorable restorability, extending (spreading) in the outward direction, at the outer circumference of blood pressure measurement bladder 50, and a belt 93 at the outer circumference of curler 92. The rotation of motor 90 causes one end of belt 93 to be wound around or unwound from reel 91. Accordingly, the inner diameter of reel squeeze portion 97 including belt 93 and curler 92 is reduced or extended. By this reduction and extension, the externally applied pressure exerted to blood pressure measurement bladder 50 via belt 93 and curler 92 is adjusted.

Specifically, reel motor 90 rotates positively when the inner diameter of reel squeeze portion 97 is to be reduced. By this positive rotation, one end of belt 93 extending from anchorage point 951 is pulled in the direction of the dotted line arrow in the drawing (other end is fixed at anchorage point 951) to be wound around reel 91, whereby belt 93 moves. This movement causes reduction in the inner diameter of curler 92, which in turn causes blood pressure measurement bladder 50 located between curler 92 and the measurement site to be wrapped around and pressed against the measurement site. In the case where the inner diameter of curler 92 is to be extended (spread), reel motor 90 rotates in the opposite direction, or the motor lock is released. At this stage, belt 93 extending from anchorage point 951 is pulled in a direction opposite to the dotted line arrow direction in the drawing. Therefore, belt 93 reeled around reel 91 is unwound, so that the inner diameter of belt 93 and curler 92 increases. This extension of the inner diameter causes blood pressure measurement bladder 50 located between curler 92 and the measurement site to be unloosened from the measurement site, so that the measurement site is relieved of pressure.

The blood pressure measurement procedure will be described with reference to FIG. 12. Steps ST1 and ST2 are carried out in a manner similar to that of electronic blood pressure measurement device 1.

Then, CPU 301 turns on motor driving circuit 461. In response, motor driving circuit 461 drives reel motor 90 based on an output signal from torque sensor 96. Accordingly, belt 93 is pulled in the direction of the dotted line arrow to cause blood pressure measurement bladder 50 to be pressed against the measurement site (step ST3*a*). At this stage, tightening is effected until a predetermined cuff level is reached, as in the previous embodiment. Then, motor drive circuit 461 rotates reel motor 90 in the opposite direction, or the lock of the motor is gradually relaxed, so that the exerting pressure in blood pressure measurement bladder 50 against the measurement site is gradually reduced. Therefore, the cuff pressure in blood pressure measurement bladder 50 is gradually reduced (ST4*a*). The process of steps ST5-ST6 is carried out in a manner similar to that described above during this reducing pressure process. Then, at step ST7*a*, a rapid discharge of blood pressure measurement bladder 50 is carried out in a manner similar to that of step ST7. At next step ST8, CPU 301 instructs motor driving circuit 461 to cause further rotation of reel motor 90 in the opposite direction. Alternatively, the lock of the motor is completely released, so that the winding of belt 93 on reel 91 is completely uncoiled. Accordingly, the inner diameter by belt 93 and curler 92 becomes so large that blood pressure measurement bladder 50 is completely detached from the measurement site. Then, the size of the inner diameter of belt 93 and curler 92 returns to the former size, and the blood pressure measurement ends.

The pulse wave envelope can be corrected in a manner similar to that of the first embodiment, even by the winding scheme of blood pressure measurement bladder 50 of the second embodiment. Therefore, blood pressure measurement can be effected accurately, independent of the circumferential size of the arm, the arm softness and the wrapping tightness.

Although belt 93 is employed for the winding member, a wire or thin plate, or the like, may be used instead.

Each embodiment has been described based on the method of measuring, after the blood pressure measurement bladder is squeezed and pressed against the measurement site, the pressure pulse wave generated in the blood pressure measurement bladder during the reducing pressure process to calculate the blood pressure value. A blood pressure value can be calculated according to similar procedures also in the increasing pressure process.

It will be understood that the embodiments of the present invention disclosed herein are by way of example only, and is not to be taken by way of limitation in all aspects. The scope of the present invention is defined, not by the description set forth above, but by the appended claims, and all changes that fall within limits and bounds of the claims, or equivalence thereof are intended to be embraced by the claims.

The invention claimed is:

1. An electronic blood pressure measurement device comprising:
   a measurement bladder for pressing against a measurement site in a state having a predetermined amount of air sealed,
   a pressure detection portion for detecting a pressure signal indicating an internal pressure in said measurement bladder,
   a squeezing portion for exerting an externally applied pressure to said measurement bladder to press said measurement site through said measurement bladder,
   a storage portion, and
   a blood pressure calculation portion, configured so that information of cuff compliance property obtained from a change of said internal pressure and volume of said measurement bladder having a predetermined amount of air sealed is stored in advance in said storage portion,
   said blood pressure calculation portion including
      a pulse wave amplitude detection portion for detecting a pulse wave amplitude included in said pressure signal detected by said pressure detection portion in a process of changing said internal pressure in said measurement bladder by changing said externally applied pressure to said measurement bladder through said squeezing portion, and
      a correction portion configured for correcting said pulse wave amplitude detected by said pulse wave amplitude detection portion using said information of cuff compliance property read out from said storage portion,
   blood pressure being calculated based on said pulse wave amplitude corrected by said correction portion.

2. The electronic blood pressure measurement device according to claim 1, wherein said correction portion includes a first correction portion configured for correcting said information of cuff compliance property stored in said storage portion so as to indicate constant cuff compliance with respect to change in said internal pressure,
   said pulse wave amplitude detected by said pulse wave amplitude detection portion being corrected according to an amount of correction of said information of cuff compliance property by said first correction portion.

3. The electronic blood pressure measurement device according to claim 1, wherein said correction portion corrects said pulse wave amplitude detected at an internal pressure lower than and higher than said internal pressure indicated by said pressure signal detected by said pressure detection portion, when a peak of said pulse wave amplitude detected at an internal pressure lower and higher than said internal pressure indicated by said pressure signal detected by said pressure detection portion is increased and decreased, respectively.

4. The electronic blood pressure measurement device according to claim 1, wherein said cuff compliance property indicates a property of the change in said volume to the change in said internal pressure being approximated to a straight line having a slope.

5. The electronic blood pressure measurement device according to claim 1, wherein said squeezing portion includes a pressing-securing air bag provided at an outer circumference of said blood pressure measurement bladder that presses against said measurement site, and having an inner diameter reduced or extended by inflation or deflation to cause change in the externally applied pressure to said blood pressure measurement bladder.

6. The electronic blood pressure measurement device according to claim 1, wherein said squeezing portion includes a band-shaped member provided at an outer circumference of said blood pressure measurement bladder that presses against said measurement portion,
   an inner diameter by said band-shaped member is reduced or extended by adjusting a tension to said band-shaped member to cause change in the externally applied pressure to said blood pressure measurement bladder.

* * * * *